US008303952B2

(12) United States Patent
Murphy et al.

(10) Patent No.: US 8,303,952 B2
(45) Date of Patent: Nov. 6, 2012

(54) METHODS FOR INDUCING IN VIVO TOLERANCE

(75) Inventors: Kenneth M. Murphy, St. Louis, MO (US); Jorn C. Albring, St. Louis, MO (US); Michelle M. Sandau, St. Louis, MO (US)

(73) Assignee: Washington University, St. Louis, MO (US)

( * ) Notice: Subject to any disclaimer, the term of this patent is extended or adjusted under 35 U.S.C. 154(b) by 40 days.

(21) Appl. No.: 12/796,392

(22) Filed: Jun. 8, 2010

(65) Prior Publication Data
US 2010/0310582 A1 Dec. 9, 2010

Related U.S. Application Data

(60) Provisional application No. 61/184,901, filed on Jun. 8, 2009.

(51) Int. Cl.
*A61K 39/395* (2006.01)

(52) U.S. Cl. .................................. 424/130.1

(58) Field of Classification Search .............. None
See application file for complete search history.

(56) References Cited

U.S. PATENT DOCUMENTS

| | | | |
|---|---|---|---|
| 7,153,950 B2 | 12/2006 | Clark | |
| 7,304,149 B2 | 12/2007 | Murphy | |
| 7,479,544 B2 | 1/2009 | Clark | |
| 7,605,229 B2 | 10/2009 | Clark | |
| 2004/0091884 A1 | 5/2004 | Clark | |
| 2004/0175380 A1* | 9/2004 | Allison et al. | 424/144.1 |
| 2005/0272118 A1* | 12/2005 | Clark et al. | 435/69.1 |
| 2007/0161061 A1 | 7/2007 | Clark | |
| 2009/0022713 A1 | 1/2009 | Clark | |
| 2009/0081229 A1 | 3/2009 | Clark | |
| 2009/0175855 A1 | 7/2009 | Clark | |
| 2009/0311280 A1* | 12/2009 | Cheung et al. | 424/185.1 |
| 2010/0104559 A1* | 4/2010 | Ware et al. | 424/130.1 |
| 2010/0172900 A1* | 7/2010 | Korman et al. | 424/133.1 |
| 2011/0230647 A1* | 9/2011 | Murphy et al. | 530/387.9 |

FOREIGN PATENT DOCUMENTS

| | | |
|---|---|---|
| AU | 2003215368 A1 | 5/2004 |
| AU | 2004325035 A1 | 5/2006 |
| BR | PI0419117 A | 12/2007 |
| CA | 2503125 A1 | 5/2004 |
| CA | 2586615 A1 | 5/2006 |
| CN | 101421298 A | 4/2009 |
| EP | 1560593 A1 | 8/2005 |
| EP | 1812465 A1 | 8/2007 |
| JP | 2006515167 T | 5/2006 |
| JP | 2008519599 T | 6/2008 |
| MX | 2007005612 A | 8/2007 |
| WO | 0202624 A2 | 1/2002 |
| WO | 0206317 A2 | 1/2002 |
| WO | 0210187 A1 | 2/2002 |
| WO | 0216429 A2 | 2/2002 |
| WO | 0216581 A2 | 2/2002 |
| WO | 02072794 A2 | 9/2002 |
| WO | 9940100 A1 | 12/2003 |
| WO | 2004000221 A3 | 12/2003 |
| WO | 2004039394 A1 | 5/2004 |
| WO | 2004096976 A3 | 11/2004 |
| WO | 2006054961 A2 | 5/2006 |
| WO | 2007001459 A3 | 1/2007 |
| WO | 2008112840 A2 | 9/2008 |

OTHER PUBLICATIONS

Schroeder et al., J. Surg. Res. 2003, 111:109-119.*
Goodnow, The Lancet 2001, 357:2115-2121.*
Check, Nature, 2007 V.447, p. 125.*
Alexander, Brief report: Chimerism and tolerance in a recipient of a deceased-donor liver transplant. New England Journal of Medicine, 2008, pp. 369-374, vol. 358.
Blazar, Blockade of programmed death-1 engagement accelerates graft-versus-host disease lethality by an IFN-gamma-dependent mechanism. Journal of Immunology, 2003, 1272-1277, Vo. 171.
Blazar, CD30/CD30 ligand (CD153) interaction regulates CD4(+) T cell-mediated graft-versus-host disease. Journal of Immunology, 2004, pp. 2933-2941, vol. 173.
Blazar, Ligation of OX40 (CD134) regulates graft-versus-host disease (GVHD) and graft rejection in allogeneic bone marrow transplant recipients. Blood, 2003, pp. 3741-3748, vol. 101.
Burton, A large array of human monoclonal antibodies to type 1 human immunodeficiency virus from combinatorial libraries of asymptomatic seropositive individuals, Proc. Natl. Acad. Sci., 1991, pp. 10134-10137, vol. 88.
Chemnitz, B and T lymphocyte attenuator-mediated signal transduction provides a potent inhibitory signal to primary human CD4 T cells that can be initiated by multiple phosphotyrosine motifs. The Journal of Immunology, 2006, pp. 6603-6614, vol. 176.
Chen, Conversion of Peripheral CD4+CD25- Naive T cells to CD4+CD25+ Regulatory T cells by TGF-beta Induction of Transcription Factor FoxP3. J Exp.Med., 2003, pp. 1875-1886, vol. 198.
Cohen, CD4(+)CD25(+) immunoregulatory T cells: New therapeutics for graft-versus-host disease. Journal of Experimental Medicine, 2002, pp. 401-406, vol. 196.
Gonzalez, A coreceptor interaction between the CD28 and TNF receptor family members B and T lymphocyte attenuator and herpesvirus entry mediator. Proc.Natl.Acad.Sci, 2005, pp. 1116-1121, vol. 102.

(Continued)

*Primary Examiner* — Ilia Ouspenski
(74) *Attorney, Agent, or Firm* — Polsinelli Shughart PC

(57) ABSTRACT

The present invention encompasses methods for inducing in vivo tolerance to a foreign tissue.

29 Claims, 9 Drawing Sheets
(1 of 9 Drawing Sheet(s) Filed in Color)

OTHER PUBLICATIONS

Gronowski, Baculovirus stimulates antiviral effects in mammalian cells. Journal of Virology, 1999, pp. 9944-9951, vol. 73.

Hoffman, Donor-type CD4(+)CD25(+) regulatory T cells suppress lethal acute graft-versus-host disease after allogeneic bone marrow transplantation. Journal of Experimental Medicine, 2002, pp. 389-399, vol. 196.

Hubbard, Absence of inducible costimulator on alloreactive T cells reduces graft versus host disease and induces Th2 deviation. Blood, 2005, pp. 3285-3292, vol. 106.

Hurchla, B and T lymphocyte attenuator exhibits structural and expression polymorphisms and is highly induced in anergic CD4(+) T cells. Journal of Immunology, 2005, pp. 3377-3385, vol. 174.

Hurchla, Unexpected role of B and T lymphocyte attenuator in sustaining cell survival during chronic allostimulation. The Journal of Immunology, 2007 pp. 6073-6082, vol. 178.

Huse, Generation of a Large Combinatorial Library of the Immunoglobulin Repertoire in Phage Lambda, Science, 1989, pp. 1275-1281, vol. 246.

Compaan, Attenuating Lymphocyte Activity The Crystal Structure of the BTLA-HVEM Complex, J Biol Chem. Nov. 25, 2005 pp. 39553-39561, vol. 280, No. 47.

Nelson, Structural Determinants of Herpesvirus Entry Mediator Recognition by Murine B and T Lymphocyte Attenuator, J Immunol. Jan. 15, 2008 pp. 940-??, vol. 180, No. 2.

Kawai, Brief report: HLA-mismatched renal transplantation without maintenance immunosuppression. New England Journal of Medicine, 2008, pp. 353-361, vol. 358.

Kohler, Continuous cultures of fused cells secreting antibody of predefined specificity, Nature, 1975, pp. 495-497, vol. 256.

Kozbor, Specific Immunoglobulin Production and Enhanced Tumorigenicity Following Ascites Growth of Human Hybridomas, J. Immunol. Methods, 1985, pp. 3142, vol. 81.

Lang, in vivo CD86 blockade inhibits CD4+ T cell activation, whereas CD80 blockade potentiates CD8+ T cell activation and CTL effector function. The Journal of Immunology, 2002, pp. 3786-3792, vol. 168.

Lepenies, Ligation of B and T lymphocyte attenuator prevents the genesis of experimental cerebral malaria. The Journal of Immunology, 2007, pp. 4093-4100, vol. 179.

Liu, Cutting Edge: A Critical Role of B and T Lymphocyte Attenuator in Peripheral T Cell Tolerance Induction. Journal of Immunology, 2009, pp. 4516-4520, vol. 182.

Morrison, Chimeric human antibody molecules: Mouse antigen-binding domains with human constant region domains, Proc. Natl. Acad. Sci., 1984, pp. 6851-6855, vol. 81.

Neuberger, Recombinant antibodies pocessing novel effector functions, Nature, 1984, pp. 604-608, vol. 312.

Ogawa, Opposing effects of anti-activation-inducible lymphocyte-immunomodulatory molecule/inducible costimulator antibody on the development of acute versus chronic graft-versus-host disease. Journal of Immunology, 2001, pp. 5741-5748, vol. 167.

Orlandi, Cloning immunoglobulin variable domains for expression by the polymerase chain reaction, Proc. Natl. Acad. Sci., 1989, pp. 3833-3837, vol. 86.

Scandling, Brief report: Tolerance and chimerism after renal and hematopoietic-cell transplantation. New England Journal of Medicine, 2008, pp. 362-368, vol. 358.

Steinberg, A crucial role for HVEM and BTLA in preventing intestinal inflammation. J Exp.Med., 2008, pp. 1463-1476, vol. 205.

Stelljes, Clinical molecular imaging in intestinal graft-versus-host disease: mapping of disease activity, prediction, and monitoring of treatment efficiency by positron emission tomography. Blood, 2008, pp. 2909-2918, vol. 111.

Takeda, Construction of chimaeric processed immunoglobulin genes containing mouse variable and human constant region sequences, Nature, 1985, pp. 452-45, vol. 314.

Tamada, Blockade of LIGHT/LT beta and CD40 signaling induces allospecific T cell anergy, preventing graft-versus-host disease. Journal of Clinical Investigation, 2002, pp. 549-557, vol. 109.

Tamada, Light, a TNF-like molecule, costimulates T cell proliferation and is required for dendritic cell-mediated allogeneic T cell response. J Immunol., 2000, pp. 4105-4110, vol. 164.

Taylor, Targeting of inducible costimulator (ICOS) expressed on alloreactive T cells down-regulates graft-versus-host disease (GVHD) and facilitates engraftment of allogeneic bone marrow (BM). Blood, pp. 3372-3380, vol. 105.

Taylor, The infusion of ex vivo activated and expanded CD4(+)CD25(+) immune regulatory cells inhibits graft-versus-host disease lethality. Blood, 2002, pp. 3493-3499, vol. 99.

Tsukada, Blockade of CD134 (OX40)-CD134L interaction ameliorates lethal acute graft-versus-host disease in a murine model of allogeneic bone marrow transplantation. Blood, 2000, pp. 2434-2439, vol. 95.

Wang, The role of herpesvirus entry mediator as a negative regulator of T cell-mediated responses. J Olin.Invest, 2005, pp. 711-717, vol. 115.

Winter, Man-made antibodies, Nature, 1991, pp. 293-299, vol. 349.

Xu, Selective targeting of the LIGHT-HVEM co-stimulatory system for the treatment of graft-versus-host disease. Blood, 2006, pp. 4097-4104, vol. 109, No. 9.

Yu, Role of CD28 in acute graft-versus-host disease. Blood, 1998, pp. 2963-2970, vol. 92.

Blazar, Infusion of anti-B7.1 (CD80) and anti-B7.2 (CD86) monoclonal antibodies inhibits murine graft-versus-host disease lethality in part via direct effects on CD4+ and CD8+ T cells. Journal of Immunology, 1996, pp. 3250-3259, vol. 157.

Cole, Mol. Cell Biol., 1984 pp. 109-120, vol. 62.

Edinger, CD4(+)CD25(+) regulatory T cells preserve graft-versus-tumor activity while inhibiting graft-versus-host disease after bone marrow transplantation. Nature Medicine, 2003, pp. 1144-1150, vol. 9.

Fontenot, Regulatory T cell lineage specification by the forkhead transcription factor FoxP3. Immunity, 2005, pp. 329-341, vol. 22.

Gavrieli, Association of Grb-2 and PI3K p85 with phosphotyrosile peptides derived from BTLA. Biochem Biophys. Res Commun., 2006, pp. 1440-1445, vol. 345.

Gavrieli, Characterization of phosphotyrosine binding motifs in the cytoplasmic domain of B and T lymphocyte attenuator required for association with protein tyrosine phosphatases SHP-1 and SHP-2. Biochem Biophys.Res Commun., 2003, pp. 1236-1243, vol. 312.

Hakim, Acute graft-versus-host reaction can be aborted by blockade of costimulatory molecules. The Journal of Immunology, 1995, pp. 1757-1766, vol. 155.

Hori, Control of regulatory T cell development by the transcription factor Foxp3. Science, 2003, pp. 1057-1061, vol. 299.

Sedy, B and T lymphocyte attenuator regulates T cell activation through interaction with herpesvirus entry mediator. Nat.Immunol., 2005, pp. 90-98, vol. 6.

Speiser, Acute graft-versus-host disease without costimulation via CD28. Transplantation, 1997, pp. 1042-1044, vol. 63.

Tamada, Modulation of T-cell-mediated immunity in tumor and graft-versus-host disease models through the LIGHT co-stimulatory pathway. Nat.Med., 2000, pp. 283-289, vol. 6.

VIA, Differential effect of CTLA4lg on murine graft-versus-host disease (GVHD) development—CTLA4lg prevents both acute and chronic GVHD development but reverses only chronic GVHD. Journal of Immunology, 1996, pp. 4258-4267, vol. 157.

Wu, B and T lymphocyte attenuator interacts with CD3zeta and inhibits tyrosine phosphorylation of TCRzeta complex during T-cell activation. Immunol Cell Biol, 2007, pp. 590-595, vol. 85, No. 8.

Cooke, An Experimental model of idiopathic pneumonia syndrome after bone narrow transplantation .1. The roles of minor H antigens and endotoxin, Blood, 1996, pp. 3230-3239, vol. 88.

Cote, Generation of human monoclonal antibodies reactive with cellular antigens, Proc. Natl. Acad. Sci. USA. Apr. 1983, pp. 2026-2030, vol. 80.

Watanabe, BTLA is a lymphocyte inhibitory receptor with similarities to CTLA-4 and PD-1, Nat. Immunol, 2003, pp. 670-679, vol. 4.

Abbas, "T-cell stimulation: an abundance of B7s", Nature Medicine, 1999, pp. 1345-1346, vol. 5, No. 12.

Anderson, "Paradoxical inhibition of T-cell function in response to CTLA-4 blockade; heterogeneity within the human T-cell population", Nature Medicine, 2000, pp. 211-214, vol. 6, No. 2.

Brodie, "LICOS, a primordial costimulatory ligand?", Current Biology, 2000, pp. 333-336, vol. 10.

Carreno, "The B7 Family of Ligands and Its Receptors: New Pathways for Costimulation and Inhibition of Immune Responses", Annu. Rev. Immunol., 2002, pp. 29-53, vol. 20.

Chambers, et al., "CTLA-4-Mediated Inhibition In Regulation of T Cell Responses: Mechanisms and Manipulation in Tumor Immunotherapy", Annu. Rev, Immunol., 2001, pp. 565-594, vol. 19.

Chanbers, "Thymocyte development is normal in CTLA-4-deficient mice", PNAS, 1997, pp. 9296-9301, vol. 94.

Chapoval, "B7-H3: A costimulatory molecule for T cell activation and IFN-γ production", Nature Immunology, 2001, pp. 269-274, vol. 2, No. 3.

Chen, "Co-Inhibitory Molecules of the B7-CD28 Family in the Control of T-Cell Immunity", Nature Review of Immunology, 2004, pp. 336-347, vol. 4.

Cheung, "Evolutionarily divergent herpesviruses modulate T cell activation by targeting the herpesvirus entry mediator cosignaling pathway", PNAS, 2005, pp. 13218-13223, vol. 102, No. 37.

Compaan, "Attenuating Lymphocyte Activity The Crystal Structure of the BTLA-HVEM Complex", Journal of Biological Chemistry, 2005, pp. 39553-39561, vol. 280, No. 47.

Connolly, "Structure-Based Analysis of the Herpes Simplex Virus Glycoprotein D Binding Site Present on Herpesvirus Entry Mediator HveA (HVEM)", Journal of Virology, 2002, pp. 10894-10904, vol. 76, No. 21.

Croft, "Co-Stimulatory members of the TNFR family: keys to effective T-cell immunity?", Nature Reviews, 2003, pp. 609-620, vol. 3.

Coyle, "The expanding B7 superfamily: Increasing complexity in costimulatory signals regulating T cell function", Nature Immunology, 2001, pp. 203-209, vol. 2, No. 3.

Damle, "Costimulation of T Lymphocytes with Intergrin Ligands Intercellular Adhesion Molecule-1 or Vascular Cell Adhesion Molecule-1 Induces Functional Expression of CTLA-4, a Second Receptor for B7", Journal of Immunology, 1994. pp. 2686-2697, vol. 152.

Dong, "B7-H1, a third member of the B7 family, co-stimulates T-cell proliferation and interleukin-10 secretion", Nature Medicine, 1999, pp. 1365-1369, vol. 5, No. 12.

Freeman, "Engagement of the PD-1 Immunoinhibitory Receptor by a Novel 67 Family Member Leads to Negative Regulation of Lymphocyte Activation", J. Exp. Med., 2000, pp. 1027-1034, vol. 192, No. 7.

Granger, "LIGHT-HVEM signaling and the regulation of T cell-mediated Immunity", Cytokine and Growth Factor Reviews, 2003, pp. 289-296, vol. 14.

Hsu, "Atar, a Novel Tumor Necrosis Factor Receptor Family Member, Signals through FRAF2 and FRAF5", The Journal of Biological Chemistry, 1997, pp. 13471-13474, vol. 272, No. 21.

Hurchla, "B and T Lymphocyte Attenuator Exhibits Structural and Expression Polymorphisms and Is Highly Induced in Anergic CD4+ T Cells", The Journal of Immunology, 2005, pp. 3377-3385, vol. 174.

Kearney, "Antigen-Dependent Clonal Expansion of a Trace Population of Antigen-Specific CD4+ T Cells In Vivo Is Dependent on CD28 Costimulation and Inhibited by CTLA-41", The Journal of Immunology, 1995, pp. 1032-1036, vol. 155.

Krummel, "CD28 and CTLA-4 Have Opposing Effects on the Response of T cells to Stimulation", J. Exp. Med., 1995, pp. 459-465, vol. 182.

Kwon, "A Newly Identified Member of the Tumor Necrosis Factor Receptor Superfamily with a Wide Tissue Distribution and Involvement in Lymphocyte Activation", The Journal of Biological Chemistry, 1997, pp. 14272-14276, vol. 272, No. 22.

Latchman, "PD-L2 is a second ligand for PD-1 and Inhibits T cell activation", Nature Immunology, 2001, pp. 261-268, vol. 2, No. 3.

Liang, "The right place at the right time: novel B7 family members regulate effector T cell responses", Current Opinion in Immunology, 2002, pp. 384-390, vol. 14.

Ling, "Cutting Edge: Identification of GL50, a Novel B7-Like Protein That Functionally Binds to ICOS Receptor", Journal of Immunology, 2000, pp. 1653-1657, vol. 164.

Mauri, "LIGHT, a New Member of the TNF Superfamily and Lymphotoxin □ Are Ligands far Herpesvirus Entry Mediator", Immunity, 1998, pp. 21-30, vol. 8.

Montgomery, "Herpes Simplex Virus-1 Entry Into Cells Mediated by a Novel Member of the TNF/NGF Receptor Family", Cell, 1996, pp. 427-436, vol. 87.

Nishimura, "PD-1: an Inhibitory immunoreceptor Involved in peripheral tolerance", TRENDS In Immunology, 2001, pp. 265-268, vol. 22, No. 5.

Peach, "Complementarily Determining Region 1 (CDR1)- and CDR3-analogous Regions in CTLA-4 and CD28 Determine the Binding to B7-1", J. Exp. Med., 1994, pp. 2049-2058, vol. 180.

Sarrias, "The three HveA receptor ligands, gD, LT-□ and LIGHT bind to distinct sites on HveA", Molecular Immunology, 2000. pp, 665-673, vol. 37.

Scheu, "Targeted Disruption of LIGHT Causes Defects in Costimulatory T Cell Activation and Reveals Cooperation with Lymphotoxin β in Mesenteric Lymph Node Genesis", J. Exp. Med., 2002, pp. 1613-1624, vol. 195, No. 12.

Sedy, "B and T lymphocyte attenuator regulates T cell activation through interaction with herpesvirus entry mediator", Nature Immunology, 2005, pp. 90-98, vol. 6, No. 1.

Sotomayor, "In vivo blockade of CTLA-4 enhances the priming of responsive T cells but fails to prevent the induction of tumor antigen-specific tolerance", PNAS, 1999, pp. 11476-11481, vol. 96.

Sun, "Characterization of Mouse and Human B7-H3 Genes", The Journal of Immunology, 2002, pp. 6294-6297, vol. 168, No. 12.

Sussman, "Activation of T Lymphocytes for the Adoptive Immunotherapy of Cancer", Annals of Surgical Oncology, 1994, pp. 296-306, vol. 1, No. 4.

Swallow, "B7h, a Novel Costimulatory Homolog of B7.1 and B7.2, Is Induced by TNF α", Immunity, 1999, pp. 423-932, vol. 11.

Tao, "Differential Effects of B and T Lymphocyte Attenuator and Programmed Death-1 on Acceptance of Partially versus Fully MHC-Mismatched Cardiac Allografts1", The Journal of Immunology, 2005, pp. 5774-5782, vol. 175.

Tseng, "B7-DC, a New Dendritic Cell Molecule with Potent Costimulatory Properties for T Cells", J. Exp. Med., 2001, pp. 839-845, vol. 193, No. 7.

Wang, "Costimulation of T cells by B7-H2, a B7-like molecule that binds ICOS", Blood, 2000, pp. 2808-2813, vol. 96.

Watanabe, "BTLA is a lymphocyte inhibitory receptor with similarities to CTLA-4 and PD-1", Nature Immunology, 2003, pp. 670-679, vol. 4, No. 7.

Whitbeck, "Glycoprotein D of Herpes Simplex Virus (HSV) Binds Directly to HVEM, a Member of the Tumor Necrosis Factor Receptor Superfamily and a Mediator of HSV Entry", Journal of Virology, 1997, pp. 6083-6093, vol. 71, No. 8.

Yang, "Enhanced Induction of Antitumor T-Cell Responses by Cytotoxic T Lymphocyte-associated Molecule-4 Blockade: The Effect Is Manifested Only at the Restricted Tumor-bearing Stages", Cancer Research, 1997, pp. 4036-4041, vol. 57.

Yoshinaga, "T-cell co-stimulation through B7RP-1 and ICOS", Nature, 1999, pp. 827-832, vol. 402.

Zhu, "Cytotoxic T lymphocyte-associated antigen 4 (CTLA-4) blockade enhances incidence and severity of experimental autoimmune neuritis in resistant mice", Journal of Neuroimmunology, 2001, pp. 111-117, vol. 115.

International Search Report dated May 22, 2007 regarding PCT/US2005/041446.

Notice of Allowance dated Jul. 19, 2007 from related U.S. Appl. No. 10/609,997, 8 pgs.

Non-final Office action dated Dec. 20, 2011 from related U.S. Appl. No. 11/875,537, 6 pgs.

Non-final Office action dated May 16, 2011 from related U.S. Appl. No. 11/875,537, 9 pgs.

Notice of Allowance dated Jun. 17, 2010 from related U.S. Appl. No. 11/875,537, 4 pgs.

Notice of Allowance dated Dec. 5, 2011 from related U.S. Appl. No. 11/719,356, 7 pgs.

Non-final Office action dated May 6, 2011 from related U.S. Appl. No. 11/719,356, 11 pgs.

Non-final Office action dated Feb. 6, 2012 from related U.S. Appl. No. 12/005,346, 8 pgs.
Bodey, Failure of Cancer Vaccines: the Significant Limitations of This Approach to Immunotherapy, Anticancer Res. 20(4):2665-2676, Jul.-Aug. 2000.
Christadoss, Animal Models of Myasthenia Gravis, Clin. Immunol. 94(2):75-87, Feb. 2000.
Dudley, Cancer Regression and Autoimmunity in Patients After Clonal Repopulation with Anti-tumor Lymphocytes, Science, 268(5594):850-854, Oct. 2002.
Egen, CTLA-4: New Insights Into Its Biological Function and Use in Tumor, Nat. Immunol. 3(7):611-618, Jul. 2002.
Gao, Tumor Vaccination That Enhances Antitumor T-cell Responses Does Not Inhibit the Growth of Established Tumors Even in Combination with Interleukin-12 Treatment: the Importance of Inducing Intratumoral T-cell Migration, J. Immunother. 23(6):643-653, 2000.
Gribben, Alloatigen and Concomitant CTLA4 Signaling Induces Clonal Deletion of Alloreative T Cells: a Novel Method to Prevent GVHD, Blood 84(1):397a, 1994.
Heslop, Cytokine Gene Transfer in the Therapy of Malignancy, Bailliere Clin. Haematol. 7(1):135-151, Mar. 1994.
Leach, Enhancement of Antitumor Immunity by CTLA-4 Blockade, Science 271(5256):1734-1739, Mar. 1996.
Lee, Increased Vaccine-specific T Cell Frequency After Peptide-based Vaccination Correlates with Increased Susceptibility to in vitro Stimulation But Does Not Lead to Tumor Regression, J. Immunol. 163(11):6292-6300, Dec. 1999.
Lewis, Growth Regulation of Human Breast and Ovarian Tumor Cells by Heregulin: Evidence of the Requirement of ErbB2 as a Critical Component in Mediating Herequlin Responsiveness, Cancer Res. 56:1457-1465, Mar. 1996.
Pardoll, Tumor Reactive T Cells Get a Boost, Nat. Biotechnol. 20(12):1207-1208, Dec. 2002.
Timmerman, Dendritic Cell Vaccines for Cancer Immunotherapy, Annu. Rev. Med. 50:507-529, 1999.
Triozzi, Clinical and Immunologic Effects of a Synthetic B-human Chorionic Gonadotropin Vaccine, Int. J. Oncol. 5:1447-1453, 1994.
Wallack, Active Specific Immunotherapy with Vaccinia Melanoma Oncolysate, Immunity 1(5):405-413, Aug. 1994.
Wang, Costimulation of T Cells by B7-H2, a B7-like Molecule That Binds ICOS, Blood 96(8):2808-2813, Oct. 2000.
Zaks, Immunization with a Peptide Epitope (p. 369-377) from HER-2/neu Leads to Peptide-specific Cytotoxic T Lymphocytes That Fail to Recognize HER-2/neu+ Tumors, Cancer Res. 58:4902-4908, Nov. 1998.
Attwood, The Babel of Bioinformatics, Science, 290:471-473, Oct. 2000.
Promega pGEM-T and pGEM-T Easy Vector Systems Technical Manual, Dec. 2005, 2 pgs.
Watanabe, BTLA is a Lymphocyte Inhibitory Receptor with Similarities to CTLA-4 and PD-1, Nature Immunology, 4 (7), 10 pgs, Jul. 2003.
Arceci, The Potential for Antitumor Vaccination in Acute Myelogenous Leukemia, J. Mol. Med. 76:80-93, 1998.
Loyet, Proteomic Profiling of Surface Proteins on Th1 and Th2 Cells, Journal of Proteome Research, Jan. 28, 2005, pp. 400-409.
Gonzalez, A coreceptor interaction betwen the CD28 and TNF receptor family members B and T lymphocyte attenuator and herpesvirus entry mediator, PNAS, Jan. 25, 2005, pp. 1116-1121, vol. 102, No. 4.
Non-final Office action dated Mar. 1, 2010 from related U.S. Appl. No. 11/875,537, 6 pgs.
Non-final Office action dated Mar. 21, 2006 from related U.S. Appl. No. 10/600,997, 21 pgs.
Non-final Office action dated Jan. 8, 2007 from related U.S. Appl. No. 10/600,997, 8 pgs.
International Search Report dated Feb. 11, 2004 from related international application No. PCT/US2003/019614, 3 pgs.
Non-final Office action dated Mar. 22, 2010 from related U.S. Appl. No. 11/719,356, 8 pgs.
Notice of Allowance dated Sep. 23, 2010 from related U.S. Appl. No. 11/875,537.
Notice of Allowance dated Oct. 28, 2010 from related U.S. Appl. No. 11/719,356.
Notice of Allowance dated Jul. 19, 2010 from related U.S. Appl. No. 11/719,356.

* cited by examiner

METHODS FOR INDUCING IN VIVO TOLERANCE

CROSS REFERENCE TO RELATED APPLICATIONS

This application claims the priority of U.S. provisional application No. 61/184,901, filed Jun. 8, 2009, which is hereby incorporated by reference in its entirety.

GOVERNMENTAL RIGHTS

This invention was made with government support under T32CA009547 and 1F32AI08006201A1 awarded by the National Institutes of Health. The government has certain rights in the invention.

FIELD OF THE INVENTION

The invention encompasses methods for inducing in vivo tolerance to a foreign tissue.

BACKGROUND OF THE INVENTION

Whereas transplantation technology of both solid organs and hematopoietic cells has the potential to cure a variety of disorders, there are still treatment-related mortalities associated with these procedures, including toxicities of chemoradiotherapy, infectious complications, and Graft-versus-Host Disease (GVHD). These related mortalities restrict the application of transplantation technology.

In GVHD, immune cells in a transplanted graft recognize the host as foreign, and mount an immune response to the host. GVHD can occur when either tissue or cells are transplanted (e.g. a solid organ or hematopoietic cells). Alternatively, a host can recognize the transplanted tissue or cell as foreign. Hence, there is a need in the art for methods of inducing in vivo tolerance to a foreign tissue or cell in a subject.

SUMMARY OF THE INVENTION

One aspect of the present invention encompasses a method for treating GVHD. The method typically comprises administering an anti-BTLA antibody to a subject at substantially the same time the subject is exposed to a graft.

Another aspect of the present invention encompasses a method for inducing in vivo tolerance to a foreign tissue in a subject. The method usually comprises administering to the subject an anti-BTLA antibody at substantially the same time as the foreign tissue exposure.

Other aspects and iterations of the invention are described more thoroughly below.

REFERENCE TO COLOR FIGURES

The application file contains at least one photograph executed in color. Copies of this patent application publication with color photographs will be provided by the Office upon request and payment of the necessary fee.

DETAILED DESCRIPTION OF THE INVENTION

Figure 1:
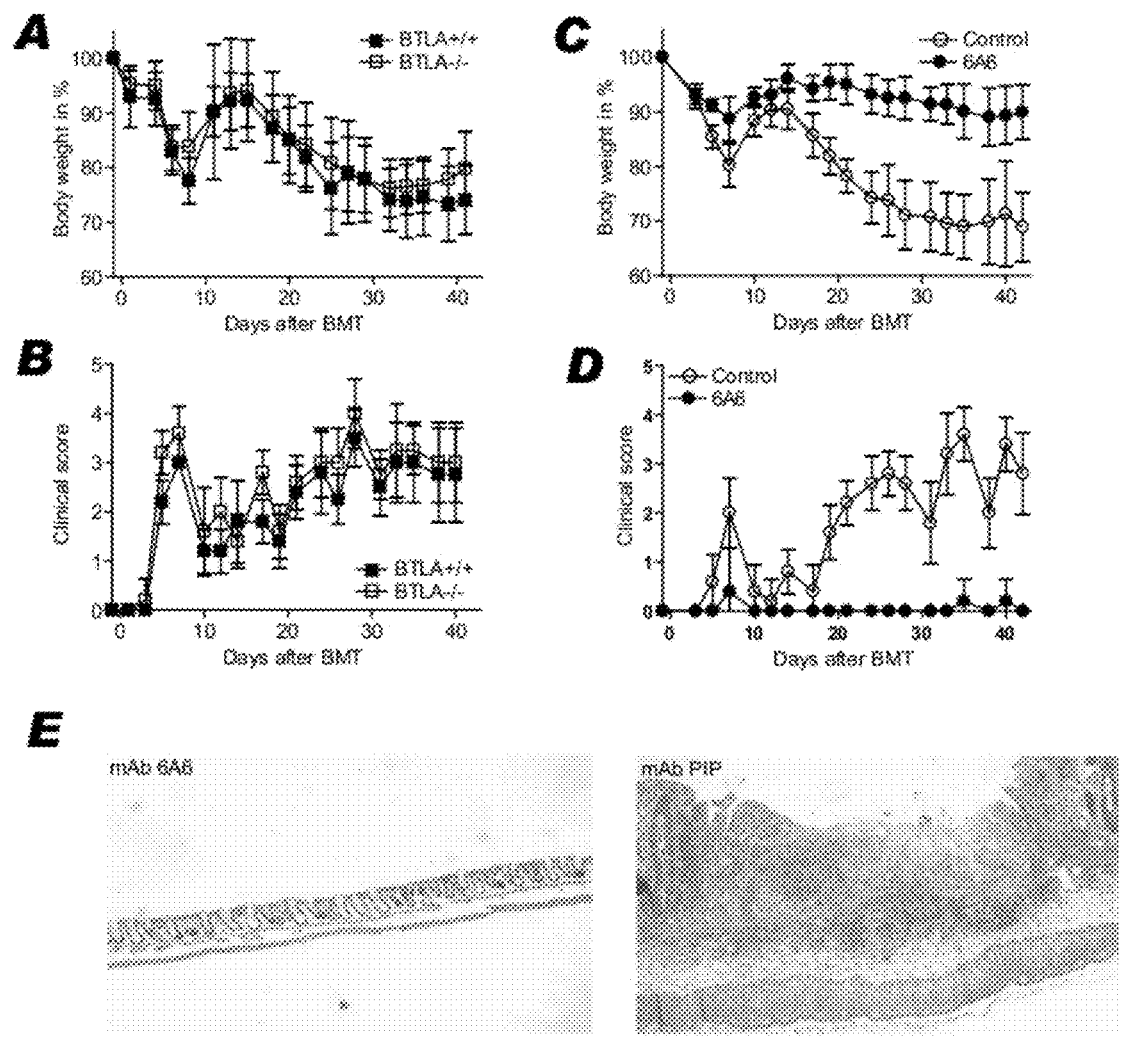
FIG. 1 depicts graphs and micrographs showing that anti-BTLA treatment permanently prevents graft-vs-host disease. CB6F1 mice were lethally irradiated and received $2.0 \times 10^7$ BMCs and $1.0 \times 10^7$ splenocytes from parental C57BL/6 BTLA+/+ (closed squares) or BTLA−/− (open squares) donors. Percent body weight (A) and clinical score (B) were measured for forty days post transplant. CB6F1 were lethally irradiated and received $2.0 \times 10^7$ BMCs and $1.0 \times 10^7$ splenocytes from parental C57BL/6 BTLA+/+ mice and a single 200 µg injection intraperitoneally of the control antibody PIP (open circles) or the antibody 6A6 (closed circles). Percent body weight (C) and clinical score (D) were measured for about forty days post transplant. Histopathology (E) of the colon 143 days after BMT of animals that had received a single injection of 6A6 (left panel) or the control antibody PIP (right panel) on the day of BMT. Original magnification for histopathology was 4×. Error bars indicate positive standard deviations for each time point. *Statistically significant differences versus both control groups (P<0.05).

The present invention provides a method of inducing in vivo tolerance to foreign tissue. In certain embodiments, a method of the invention may induce in vivo tolerance without causing substantial systemic immune suppression in the host. Such a method may be used, in part, to prevent and/or treat GVHD. Generally speaking, the method comprises administering an anti-BTLA antibody to a subject exposed to foreign tissue. Typically, the anti-BTLA antibody administration occurs at substantially the same time as the foreign tissue exposure. In exemplary embodiments, only one dose of an antibody is administered.

I. Methods for Inducing In Vivo Tolerance

The present invention encompasses a method for inducing in vivo tolerance to foreign tissue. The method typically comprises administering an anti-BTLA antibody to a subject at substantially the same time the subject is exposed to the foreign tissue. As used herein, "in vivo tolerance" refers to the substantial lack of immune response specific for the foreign tissue. The immune response may stem from the recipient subject mounting an immune response to a foreign tissue, or conversely, the immune response may stem from the foreign tissue mounting an immune response to the recipient subject (e.g. GVHD). Methods of measuring in vivo tolerance are commonly known in the art.

Suitable subjects have been, or will be, exposed to a foreign tissue. The term "foreign tissue," as used herein, may encompass a bone marrow transplant, an organ transplant, a blood transfusion, or any other foreign tissue or cell that is purposefully introduced into a subject.

In certain embodiments, a method of the invention may be used to induce in vivo tolerance without causing substantial systemic immune suppression in the host. Methods of detecting substantial systemic immune suppression are known in the art, and may include, for example, measuring and detecting the ability of the host immune cells to respond to a stimulus in vitro.

In one embodiment, the present invention encompasses a method for treating graft v. host disease (GVHD). Generally speaking, a method of the invention typically comprises administering an anti-BTLA antibody to a subject at risk for GVHD at substantially the same time the subject is exposed to the graft. A subject at risk for GVHD, generally speaking, is a subject exposed to a graft comprising viable and functional immune cells, where the graft is not 100% histocompatible with the subject. In some embodiments, the subject is immunocompromised. In an exemplary embodiment, the subject is human.

As used herein, "treating" refers to preventing GVHD or ameliorating GVHD symptoms in a subject. For instance, in one embodiment, treating GVHD refers to substantially preventing GVHD associated weight loss. In another embodiment, treating GVHD means that there is no detectable cellular infiltrate in a target organ after the host is exposed to the foreign tissue. Suitable target organs in the context of GVHD may include the liver, skin and mucosa, the gastrointestinal tract, the bone marrow, the thymus, and the lungs.

In yet another embodiment, treating GVHD refers to decreasing the clinical score of the subject. For instance, in mice evidence of GVHD may be scored by assessing five clinical parameters: weight loss, posture (hunching), activity, fur texture, and skin integrity. Individual mice receive a score of 0 to 2 for each criteria (maximum score of 10). See Table A below.

TABLE A

| Criteria | Grade 0 | Grade 1 | Grade 2 |
|---|---|---|---|
| Weight loss | <10% | >10% to <25% | >25% |
| Posture | Normal | Hunching noted | Severe hunching |
| Activity | Normal | Mild to moderately decreased | Stationary unless stimulated |
| Fur texture | Normal | Mild to moderate ruffling | Severe ruffling/ poor grooming |
| Skin integrity | Normal | Scaling of paws/tail | Obvious areas of denuded skin |

Analogously, in humans clinical scoring of acute GVHD may be performed by assessing three parameters (skin findings, liver findings (Bilirubin level, mg/dL), and gut findings) using the staging highlighted in Table B below. Overall clinical scoring of acute GVHD in humans may then be calculated using Table C below:

TABLE B

| Stage | Skin Findings | Liver Findings (Bilirubin level, mg/dL) | Gut Findings |
|---|---|---|---|
| + | Maculopapular rash on <25% of body surface | 2-3 | Diarrhea 500-1000 mL/d or persistent nausea |
| ++ | Maculopapular rash on 25-50% of body surface | 3-6 | Diarrhea 1000-1500 mL/d |
| +++ | Generalized erythroderma | 6-15 | Diarrhea >1500 mL/d |
| ++++ | Desquamation and bullae | >15 | Pain with or without ileus |

TABLE C

| | Stage | | | |
|---|---|---|---|---|
| Overall Grade | Skin | Liver | Gut | Functional Impairment |
| 0 (None) | 0 | 0 | 0 | 0 |
| I (Mild) | + to ++ | 0 | 0 | 0 |
| II (Moderate) | + to +++ | + | + | + |
| III (Severe) | ++ to +++ | ++ to +++ | ++ to +++ | ++ |
| IV (Life-threatening) | ++ to ++++ | ++ to ++++ | ++ to ++++ | +++ |

In some embodiments, a method of the invention may comprise decreasing the clinical score of a subject, from, for example, a IV to a III, a III to a II, a II to a I, or a I to a 0 when the subject is human. In other embodiments, a method of the invention may comprise decreasing the clinical score of a subject, from, for example, 10 to 9, 9 to 8, 8 to 7, 7 to 6, 6 to 5, 5 to 4, 4 to 3, 3 to 2, 2 to 1, or 1 to 0 when the subject is a mouse.

Generally speaking, if a method of the invention is used to decrease the clinical GVHD score of a subject, the decrease may be calculated with respect to either A) the difference between a first score calculated within 10, 9, 8, 7, 6, 5, 4, 3, 2, or 1 days of the foreign tissue exposure and a second score calculated after treatment of the subject with an anti-BTLA antibody, or B) the difference between a first score calculated within 10, 9, 8, 7, 6, 5, 4, 3, 2, or 1 days of the foreign tissue exposure (in a subject treated with anti-BTLA antibody) and a typical baseline score of a control subject exposed to a foreign tissue without anti-BTLA antibody treatment.

(a) anti-BTLA Antibody

A method of the invention encompasses administering an anti-BTLA antibody. Generally speaking, the anti-BTLA antibody is capable of binding to BTLA and initiating the expansion of a pre-existing pool of Treg cells. In some embodiments, the anti-BTLA antibody does not deplete T cells expressing BTLA. In other embodiments, the anti-BTLA antibody does not fix complement. In certain embodiments, the anti-BTLA antibody recognizes the same epitope as the anti-BTLA antibody 6A6. The 6A6 anti-BTLA antibody is commonly known in the art. In certain other embodiments, the anti-BTLA antibody recognizes amino acid epitopes on the surface of BTLA that interacts with HVEM. This surface is generally conserved in humans and mice. (See J Biol Chem. 2005 Nov. 25; 280(47):39553-61 and J. Immunol. 2008 Jan. 15; 180(2):940-7, each of which is hereby incorporated by reference in their entirety). For instance, the anti-BTLA antibody may recognize the Q27, C49, and Q66 amino acids of mouse BTLA. In each of the above embodiments, the constant region of the antibody may be human.

An antibody of the invention may be generated using BTLA, or a fragment thereof, as an immunogen using methods that are well known in the art. Identification and selection of an antibody that binds to BTLA may be performed using methods commonly known in the art. For more details, see the Examples.

Usually, an anti-BTLA antibody of the invention is a monoclonal antibody. Monoclonal antibodies that bind to BTLA may be prepared using a technique that provides for the production of antibody molecules by continuous cell lines in culture. These include, but are not limited to, the hybridoma technique, the human B-cell hybridoma technique, and the EBV-hybridoma technique. (See, e.g., Kohler, G. et al. (1975) Nature 256:495-497; Kozbor, D. et al. (1985) J. Immunol. Methods 81:3142; Cote, R. J. et al. (1983) Proc. Natl. Acad. Sci. USA 80:2026-2030; and Cole, S. P. et al. (1984) Mol. Cell Biol. 62:109-120.)

In addition, techniques developed for the production of "chimeric antibodies," such as the splicing of mouse antibody genes to human antibody genes to obtain a molecule with appropriate antigen specificity and biological activity may be used. (See, e.g., Morrison, S. L. et al. (1984) Proc. Natl. Acad. Sci. USA 81:6851-6855; Neuberger, M. S. et al. (1984) Nature 312:604-608; and Takeda, S. et al. (1985) Nature 314:452-45). Alternatively, techniques described for the production of single chain antibodies may be adapted, using methods known in the art, to produce single chain antibodies that bind to BTLA. Antibodies with related specificity, but of distinct idiotypic composition, may be generated by chain shuffling from random combinatorial immunoglobulin libraries. (See, e.g., Burton, D. R. (1991) Proc. Natl. Acad. Sci. USA 88:10134-10137.)

Antibodies may also be produced by inducing in vivo production in the lymphocyte population or by screening immunoglobulin libraries or panels of highly specific binding reagents as disclosed in the literature. (See, e.g., Orlandi, R. et al. (1989) Proc. Natl. Acad. Sci. USA 86:3833-3837; Winter, G. et al. (1991) Nature 349:293-299.)

Antibody fragments that contain specific binding sites for BTLA or fragments thereof may also be generated. For example, such fragments include, but are not limited to, F(ab')2 fragments produced by pepsin digestion of the antibody molecule and Fab fragments generated by reducing the disulfide bridges of the F(ab')2 fragments. Alternatively, Fab expression libraries may be constructed to allow rapid and easy identification of monoclonal Fab fragments with the desired specificity. (See, e.g., Huse, W. D. et al. (1989) Science 246:1275-1281.)

In the production of antibodies, screening for the desired antibody may be accomplished by techniques known in the art, e.g. ELISA (enzyme-linked immunosorbent assay). Various immunoassays may be used for screening to identify antibodies having the desired specificity. Numerous protocols for competitive binding or immunoradiometric assays using either polyclonal or monoclonal antibodies with established specificities are well known in the art. Such immunoassays typically involve the measurement of complex formation between BTLA and its specific antibody.

In some embodiments of the invention, an antibody may be conjugated to a complex, such as a therapeutic complex or an imagining complex. Methods of conjugating antibodies to various complexes are known in the art. In other embodiments, an antibody of the invention may be labeled with a detectable marker. The marker may be either non-covalently or covalently joined to an antibody of the present invention by methods generally known in the art. Detectable markers suitable for use in the invention generally comprise a reporter molecule or enzyme that is capable of generating a measurable signal. By way of non-limiting example, such detectable markers may include a chemiluminescent moiety, an enzymatic moiety (e.g. horse-radish peroxidase), a fluorescent moiety (e.g. FITC) or a radioactive moiety. Additionally, in some embodiments, an antibody of the invention may be labeled with avidin or biotin.

(b) Administration

Generally speaking, an anti-BTLA antibody is administered at substantially the same time the subject is exposed to the foreign tissue. As used herein, "substantially the same time" means that the antibody is administered close enough to the foreign tissue exposure to achieve a suppressive environment of alloreactive T cells. In one embodiment, the anti-BTLA antibody is administered at the same time as the foreign tissue exposure. In another embodiment, the anti-BTLA antibody is administered before the foreign tissue exposure. In yet another embodiment, the anti-BTLA antibody is administered after foreign tissue exposure. In exemplary embodiments, the antibody is administered close enough to the foreign tissue exposure to treat GVHD. In other exemplary embodiments, the antibody is administered close enough to the foreign tissue exposure to induce in vivo tolerance.

An anti-BTLA antibody may be administered to the subject once, or more than once. For instance, an anti-BTLA antibody may be administered 1, 2, 3, 4, 5, 6, 7, 8, 9, 10, or more than 10 times. By way of non-limiting example, an anti-BTLA antibody may be administered at the time of the foreign tissue exposure, and after foreign tissue exposure. Alternatively, an anti-BTLA antibody may be administered before foreign tissue exposure and at the time of foreign tissue exposure. In another alternative, an anti-BTLA antibody may be administered before and after foreign tissue exposure. In still another alternative, an anti-BTLA antibody may be administered before foreign tissue exposure, at the time of foreign tissue exposure, and after foreign tissue exposure.

Generally speaking, in each of the above embodiments, an anti-BTLA antibody may be administered within 10 days of exposure to a foreign tissue. For instance, an anti-BTLA antibody may be administered 10, 9, 8, 7, 6, 5, 4, 3, 2, or 1 days before foreign tissue exposure, and/or 10, 9, 8, 7, 6, 5, 4, 3, 2, or 1 days after foreign tissue exposure. In some embodiments, an anti-BTLA antibody may be administered within a week of exposure to a foreign tissue.

Usually, the amount of anti-BTLA antibody administered is between about 5 µg/g body weight to about 20 µg/g body weight. In some embodiments, the amount of anti-BTLA antibody administered is about 5, 6, 7, 8, 9, 10, 11, 12, 13, 14, 15, 16, 17, 18, 19 or 20 µg/g body weight.

An antibody of the invention may be incorporated into a pharmaceutical composition suitable for administration to a subject. Typically, the pharmaceutical composition comprises an antibody or antibody fragment of the invention and a pharmaceutically acceptable carrier. As used herein, "pharmaceutically acceptable carrier" includes any and all solvents, dispersion media, coatings, antibacterial and antifungal agents, isotonic and absorption delaying agents, and the like that are physiologically compatible. Examples of pharmaceutically acceptable carriers include one or more of water, saline, phosphate buffered saline, dextrose, glycerol, ethanol and the like, as well as combinations thereof. In many cases, it will be preferable to include isotonic agents, for example, sugars, polyalcohols such as mannitol, sorbitol, or sodium chloride in the composition. Pharmaceutically acceptable carriers may further comprise minor amounts of auxiliary substances such as wetting or emulsifying agents, preservatives or buffers, which enhance the shelf life or effectiveness of the antibody or antibody portion.

The pharmaceutical compositions of this invention may be in a variety of forms. These include, for example, liquid, semi-solid and solid dosage forms, such as liquid solutions (e.g., injectable and infusible solutions), dispersions or suspensions, tablets, pills, powders, liposomes and suppositories. The preferred form depends on the intended mode of administration and therapeutic application. Typical preferred compositions are in the form of injectable or infusible solutions, such as compositions similar to those used for passive immunization of humans with other antibodies. The preferred mode of administration is parenteral (e.g., intravenous, subcutaneous, intraperitoneal, intramuscular). In a preferred embodiment, the antibody is administered by intravenous infusion or injection. In another preferred embodiment, the antibody is administered by intramuscular or subcutaneous injection.

Pharmaceutical compositions may be sterile and are typically stable under the conditions of manufacture and storage. The composition may be formulated as a solution, microemulsion, dispersion, liposome, or other ordered structure suitable to high drug concentration. Sterile injectable solutions can be prepared by incorporating the active compound (i.e., antibody or antibody fragment) in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those detailed above. In the case of sterile powders for the preparation of sterile injectable solutions, the preferred methods of preparation are vacuum drying and freeze-drying that yields a powder of the active ingredient plus any additional desired ingredient from a previously sterile-filtered solution thereof. The proper fluidity of a solution may be maintained, for example, by the use of a coating such as lecithin, by the maintenance of the required particle size in the case of dispersion and by the use of surfactants. Prolonged absorption of injectable compositions may be achieved by including an agent that delays absorption, for example, monostearate salts and gelatin, in the composition.

An antibody of the invention, or a pharmaceutical composition comprising an antibody of the invention, may be administered to a subject. An antibody of the present invention may be administered by a variety of methods known in the art, although for many therapeutic applications, the preferred route/mode of administration is intravenous injection or infusion. As will be appreciated by the skilled artisan, the route and/or mode of administration will vary depending upon the desired results. In certain embodiments, the active compound may be prepared with a carrier that will protect the compound against rapid release, such as a controlled release formulation, including implants, transdermal patches, and microencapsulated delivery systems. Biodegradable, biocompatible polymers may be used, such as ethylene vinyl acetate, polyanhydrides, polyglycolic acid, collagen, polyorthoesters, and polylactic acid. Many methods for the preparation of such formulations are patented or generally known to those skilled in the art. See, e.g., Sustained and Controlled Release Drug Delivery Systems, J. R. Robinson, ed., Marcel Dekker, Inc., New York, 1978.

In certain embodiments, an antibody of the invention may be orally administered, for example, with an inert diluent or an assimilable edible carrier. The composition (and other ingredients, if desired) may also be enclosed in a hard or soft shell gelatin capsule, compressed into tablets, or incorporated directly into the subject's diet. For oral therapeutic administration, the compounds may be incorporated with excipients and used in the form of ingestible tablets, buccal tablets, troches, capsules, elixirs, suspensions, syrups, wafers, and the like. To administer a compound of the invention by other than parenteral administration, it may be necessary to coat the compound with, or co-administer the compound with, a material to prevent its inactivation.

The following examples are included to demonstrate preferred embodiments of the invention. It should be appreciated by those of skill in the art that the techniques disclosed in the examples that follow represent techniques discovered by the inventors to function well in the practice of the invention. Those of skill in the art should, however, in light of the present disclosure, appreciate that many changes can be made in the specific embodiments that are disclosed and still obtain a like or similar result without departing from the spirit and scope of the invention, therefore all matter set forth or shown in the accompanying drawings is to be interpreted as illustrative and not in a limiting sense.

EXAMPLES

The following examples illustrate various iterations of the invention.

Introduction

Allogeneic replacement of an abnormal or malignant hematopoietic system by allogeneic hematopoietic stem-cell transplantation (aHSCT) from a healthy donor can cure a variety of blood cell disorders and induce long-lasting tolerance to foreign tissues (1-3). The high treatment-related mortality of this procedure due to toxicities of chemoradiotherapy, infectious complications, and Graft-versus-Host Disease (GVHD), however, restricts its widespread application. Thus it is necessary to develop new methods for inhibiting GVHD, while maintaining the positive effects of donor T cells for the broader application of aHSCT in patients with inherited disorders of hematopoiesis (such as sickle cell anemia or aplastic anemia) or patients without an MHC-matched donor. The regulation of multiple costimulatory molecules on donor-derived T cells is crucial to the outcome of GVHD. Stimulation of co-inhibitory molecules ameliorates GVHD, while co-stimulatory molecules lead to the pathogenesis of GVHD. In addition to the CD28 family of co-stimulatory molecules (4-12), functional roles for the TNF receptor family of co-stimulatory ligands and receptors has been implicated in the pathogenesis of GVHD (13-20). Here it is shown that a single administration of a non-depleting monoclonal antibody directed against BTLA (22) after aHSCT leads to the expansion of regulatory T cells and the permanent prevention of GVHD. Thus, targeting BTLA could improve the safety of aHSCT and broaden its application to common non-life threatening diseases. In addition, targeting BTLA may induce tolerance to solid organ grafts.

Example 1

BTLA is not normally engaged during GVHD

To determine whether BTLA signaling played a functional role in the development GVHD, wild type and BTLA-deficient mice (23) were first examined using a parental into irradiated F1 model. In this model GVHD manifests as a result of a partial MHC mismatch achieved through parental donor cells of the H-$2^b$ haplotype and the lethally irradiated recipients of the H-$2^{b/d}$ haplotype. Bone marrow and splenocytes from either wildtype or BTLA−/− were transferred into lethally irradiated CB6F1 recipients (FIG. 1A). As expected, transplantation of wild type donor cells into CB6F1 recipients caused a decrease in body weight of approximately 30%, and generated clinical scores (24) of about 3 which persisted for greater than 40 days (FIG. 1B). BTLA−/− donor cells caused GVHD to a similar magnitude as wild type donor cells (FIGS. 1A & B).

Figure 2:
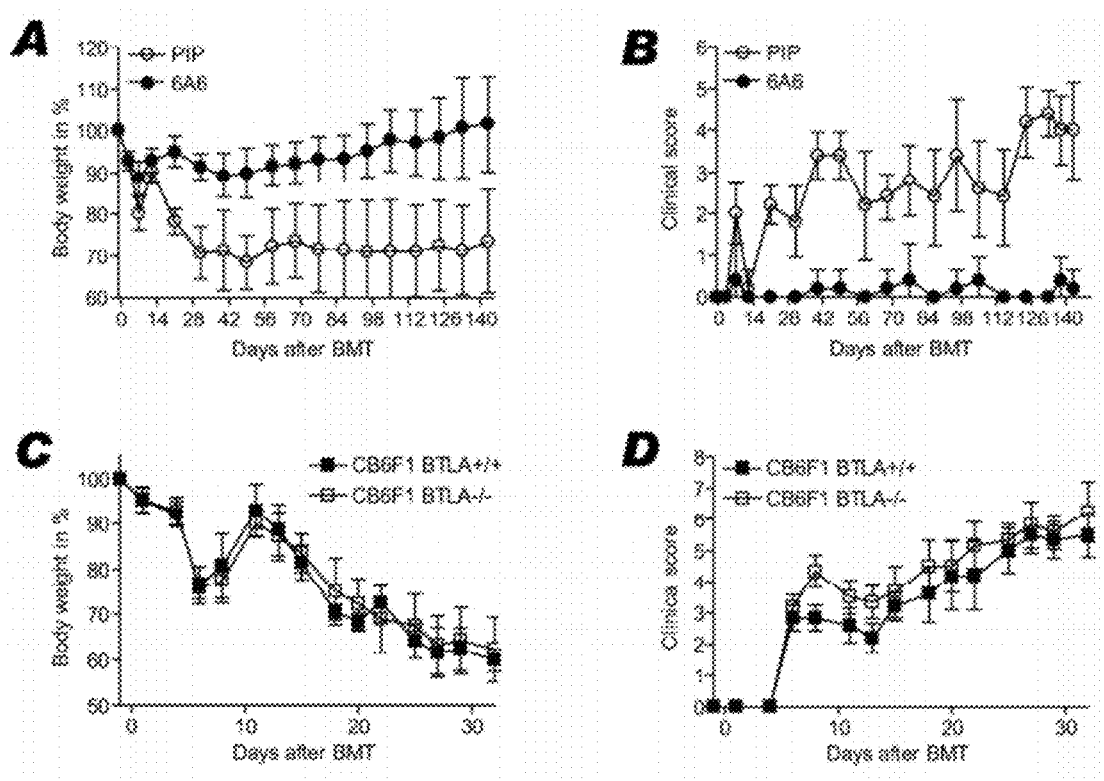
FIG. 2 depicts a series of graphs showing BTLA expression by recipient tissue does not promote GVHD, but anti BTLA treatment prevents GVHD long term. A & B represent the same experiment as in FIGS. 1C & D extended for 143 days. Body weight loss (A) and a clinical score (B) were used as a measure of GVHD in recipient mice after BMT. Error bars indicate positive standard deviations for each time point. CB6F1 BTLA+/+ mice (closed squares) or CB6F1 BTLA−/− (open squares) were lethally irradiated and received $2.0 \times 10^7$ BMCs and $1.0 \times 10^7$ splenocytes from parental C57BL/6 BTLA−/− donors. Body weight loss (C) and a clinical score (D) were used as a measure of GVHD in recipient mice after BMT.

To determine if recipient expression of BTLA played a role in GVHD we transferred either wildtype or BTLA−/− bone marrow and splenocytes into lethally irradiated BTLA−/− CB6F1 hosts (FIG. 2). Donor cells from both wild type and BTLA−/− caused similar disease in the BTLA−/− hosts, as they displayed similar weight loss and GVHD clinical scores as compared to BTLA+/+ recipients (FIG. 1). Collectively these data suggest that BTLA is not normally engaged by either donor or recipient cells during the pathophysiological process of developing GVHD.

Example 2

Anti-BTLA Antibody Prevent GVHD

Since BTLA provides inhibitory signaling (23, 25, 26) and is active during several immunoregulatory models (27) (including infectious diseases such as malaria (28)), we tested whether direct engagement of BTLA during bone marrow transplantation could regulate the development of GVHD. To test this hypothesis, we used an anti-BTLA monoclonal antibody, 6A6 (22; herein incorporated by reference in its entirety), delivered at the time of bone marrow transplantation (FIG. 1B). As a control, an irrelevant antibody that recognizes bacterial GST (PIP) was used (29). Treatment with the control Ab had no effect on GVHD progression, and mice receiving control antibody showed progression of disease similar to that of mice receiving wild type donor cells without treatment (FIG. 1A). Furthermore, mice receiving control antibody showed persistent GVHD up to 140 days, with clinical scores between 3 and 4 for this entire period (FIGS. 2A & B). In contrast, transplantation of wild type donor cells with a single treatment using 200 ug of 6A6 led to a complete prevention of GVHD with initial weight loss less than 10%, and no clinical signs of disease (FIGS. 1C & D). This treatment led to long term prevention of GVHD as no signs of clinical disease developed at any time up to 140 days after BMT (FIG. 2).

The colon is a major target organ of GVHD in this model (30) and recipient mice treated with the control antibody developed typical signs of GVHD, with massive thickening of the lamina propria, muscular layers and intense inflammatory infiltrates and ulceration (FIG. 1E left panel). By contrast, histological analysis of the colon from mice that received 6A6 treatment revealed essentially normal architecture with no cellular infiltrates into the lamina propria or epithelium. These data suggest a single administration of anti-BTLA antibody prevents GVHD long term as defined by no weight loss, low clinical GVHD score and no detectable cellular infiltrate in a target organ such as the colon.

Example 3

Substantially Delayed Antibody Administration does not Prevent GVHD

Figure 3:
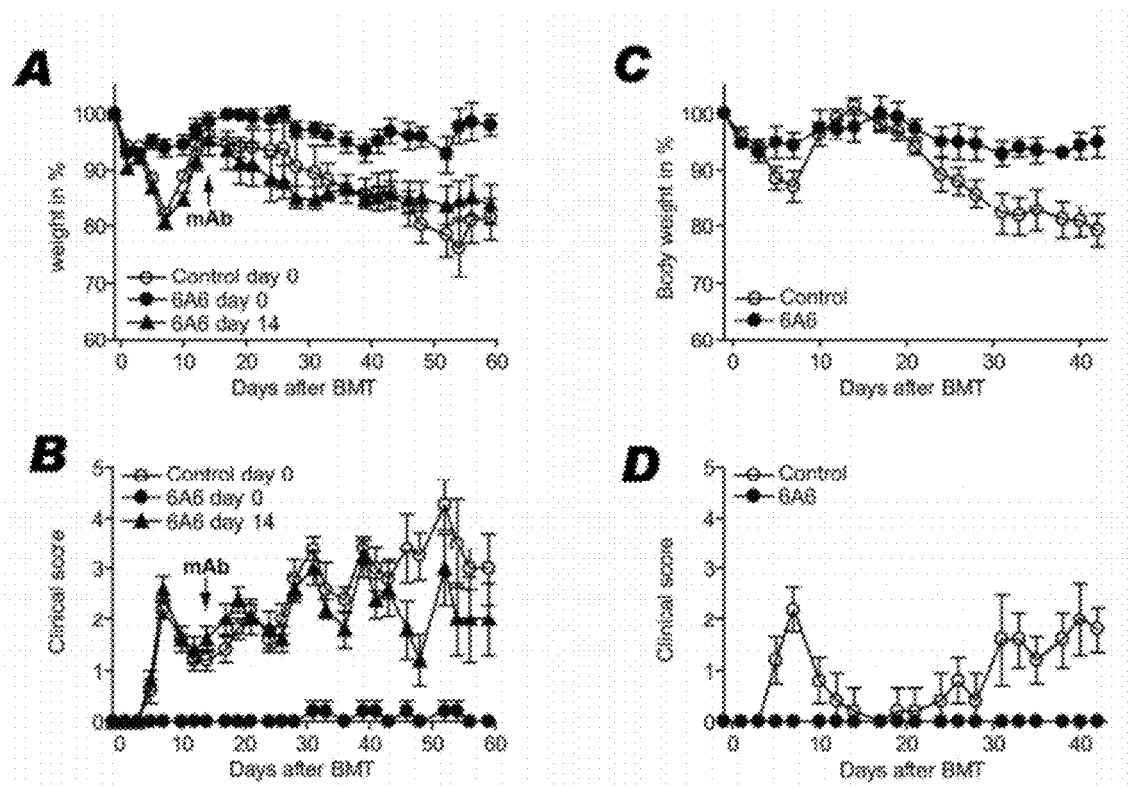
FIG. 3 depicts a series of graphs showing that anti BTLA treatment exerts its affects at the time of BMT and independent from BTLA-HVEM interactions. CB6F1 mice were lethally irradiated and received $2.0 \times 10^7$ BMCs and $1.0 \times 10^7$ splenocytes from parental C57BL/6 BTLA+/+ mice together with either a single 200 µg injection intraperitoneally of control antibody (open circles) or 6A6 (closed circles) on the day of BMT or a single 200 µg injection of 6A6 14 days after BMT (triangles). Body weight loss (A) and a clinical score (B) were used as a measure of GVHD in recipient mice after BMT. CB6F1 were lethally irradiated and received $2.0 \times 10^7$ BMCs and $1.0 \times 10^7$ splenocytes from parental C57BL/6 HVEM−/− mice and a single 200 µg injection intraperitoneally of control antibody PIP (open circles) or 6A6 (closed circles). Body weight loss (C) and a clinical score (D) were used as a measure of GVHD in recipient mice after BMT. Error bars indicate positive standard deviations for each time point. *Statistically significant differences versus both control groups (P<0.05).

Since the single administration of 6A6 permanently prevented the development of GVHD in this system, it was tested whether BTLA treatment by 6A6 could either reverse or prevent disease if administered at a substantially later point in time. Therefore the experiments were repeated using administration of 6A6 at day 14 following BMT (FIG. 3A). Administration of 6A6 at the time of transplantation did prevent disease, as expected, however substantially delayed administration of 6A6 did not cure GVHD. There was no statistical difference between the weight loss or the clinical score between control mice that received no antibody, or mice that received 6A6 on day 14 after BMT, suggesting that substantially delayed administration has no effect on preventing GVHD.

Example 4

Antibody Mechanism is Independent of HVEM Interaction

Because BTLA binds to HVEM (31, 32), a member of the TNF receptor family, it was possible that the prevention of GVHD seen after 6A6 administration was due to interference with BTLA and HVEM interactions in the host. If this were true, then 6A6 should have no curative effects when HVEM−/− donor cells were transplanted. HVEM−/− donor cells cause GVHD, when the control antibody PIP was administered (FIG. 3D). However, GVHD caused by HVEM−/− donor cells is prevented by treatment with 6A6 at the time of transplantation. Interestingly, the degree of weight loss and the clinical scores are somewhat reduced when HVEM−/− donor cells (FIG. 3D) induce GVHD compared to wild type donor cells (FIG. 1B), consistent with a recent report that HVEM and LIGHT act as co-stimulatory molecules promoting pathophysiology in GVHD (16). These results demonstrate that the curative effects of 6A6 on GVHD operate in a manner that is independent of HVEM, consistent with an active signal through BTLA on donor cells.

Example 5

Antibody does not Deplete T Cells

Figure 4:
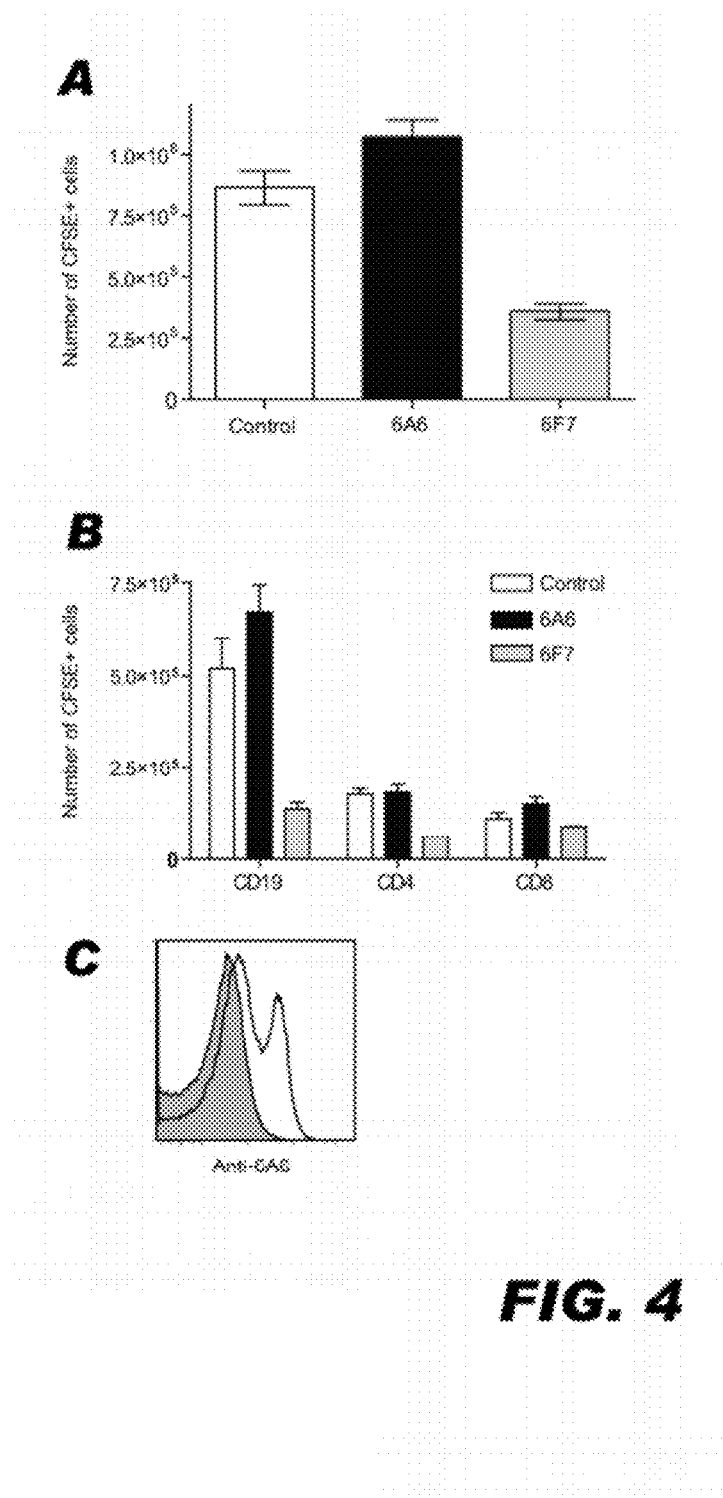
FIG. 4 depicts a series of graphs showing that anti-BTLA antibody 6A6 does not deplete lymphocytes. C57BL/6 mice received $5.0 \times 10^6$ CFSE-labeled splenocytes from B6.SJL mice together with a single 200 µg injection intraperitoneally of either control antibody or anti-BTLA antibodies 6A6, 6F7. After 2 days splenocytes were stained for CD4, CD8, CD19, and anti-hamster (for 6A6 and PIP). Shown are numbers of either all donor CFSE+ cells (A) or CD19+, CD8+, and CD4+ subsets of CFSE+ cells (B) recovered from mice that had received either control antibody (open bars), 6A6 (filled bars) or 6F7 (shaded bars). Data shown are mean±SEM (n=3). (C) CB6F1 (CD45.1−) mice were lethally irradiated and received $5.0 \times 10^7$ splenocytes from B6.SJL (CD45.1+) mice together with a single 200 µg injection intraperitoneally of either 6A6 or PIP. After 7 days splenocytes were stained for CD45.1 and anti-hamster. Shown is a histogram detecting bound antibody to lymphocytes read out by anti-hamster intensity within the 45.1+ donor cell population of mice that had either received 6A6 (bold line) or PIP (shaded fill).

6A6 treatment leads to a drastic prevention in GVHD, therefore it was determined whether 6A6 exerted its effects simply by depletion of donor T cells that expressed BTLA. Wildtype donor cells were labeled with CFSE and transferred into wildtype recipients. At the time of transfer mice were treated with control antibody PIP, anti-BTLA 6A6 or anti-BTLA 6F7. Two days after transfer similar numbers of total CFSE+ cells, as well as lymphocytes CD19+, CD4+ and CD8+ cells were recovered from mice that received either control antibody PIP or anti-BTLA 6A6 (FIG. 4A). In contrast, anti-BTLA antibody 6F7 lead to a depletion of lymphocytes, most drastically CD19+ cells as they express the highest levels of BTLA. Furthermore, we were able to detect 6A6 bound to donor derived cells 7 days after transfer where various levels of bound 6A6 is detected and is likely the demonstration of BTLA high cellular expression of BTLA on B cells compared to T cells (FIG. 4B). Thus 6A6 is not a depleting antibody. This is likely because it is an IgG1 hamster monoclonal antibody and is unlikely to fix mouse compliment, whereas anti-BTLA antibody 6F7 mediates significant lymphocyte depletion because it is a IgGK mouse monoclonal antibody (22).

Example 6

Antibody Mechanism is via Treg Population

Figure 5:
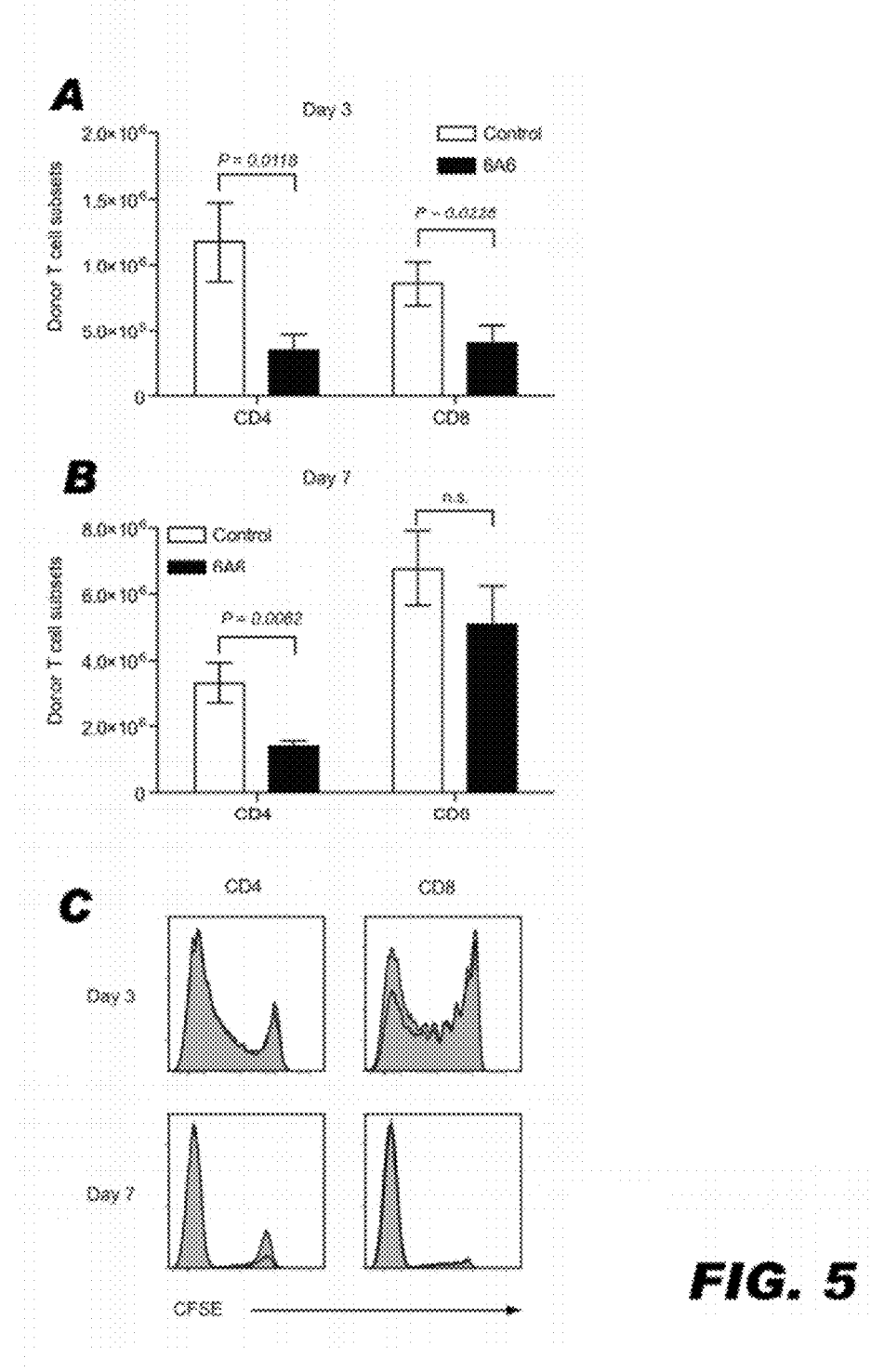
FIG. 5 depicts a series of graphs showing that CD4 T cell accumulation is modestly affected by 6A6 treatment while CD4 and CD8 T cell proliferation is unperturbed. CB6F1 (CD45.1−) mice were lethally irradiated and received 5.0× $10^7$ CFSE-labeled splenocytes from B6.SJL (CD45.1+) mice together with a single 200 µg injection intraperitoneally of either the antibody 6A6 or the control antibody PIP. After 3 (A) and 7 (B) days splenocytes were stained for CD45.1, CD4, and CD8. Shown are numbers of CD4+ (left) or CD8+ (right) cells of the 45.1+ donor cell population recovered from mice that had received either 6A6 (open bars) or PIP (filled bars). Data shown are mean±SEM (n=3). (C) Histograms of cell division history indicated by CFSE-intensity for CD4+ (left) or CD8+ (right) cells within the 45.1+ donor cell population on days 3 (upper panel) and 7 (lower panel) of mice that had either received 6A6 (bold line) or PIP (shaded fill).

BTLA signaling in T cells generally provides an inhibitory signal (23, 25, 26), however the precise mechanisms of this inhibition, the molecules involved, and the targets of inhibition are still somewhat obscure (25, 33, 34). It has been shown that BTLA engagement with HVEM leads to a decrease in cell proliferation in vitro (31). In addition BTLA deficient T cells are less likely to become anergic (35). Therefore it was sought to determine whether 6A6 engagement results in a decrease in proliferation or IL-2 production by T cells. We CFSE labeled donor splenocytes and transferred them into lethally irradiated CB6F1 recipients and treated with either control or 6A6 antibody to asses the proliferation rate following BMT. CD4 and CD8 T cell proliferation 3 and 7 days after transfer was similar between mice that received control antibody and 6A6. This was demonstrated by similar cell division history profiles with CFSE dilution (FIG. 5C). The cellular expansion of donor CD8 T cells in mice treated with 6A6 resulted in a 50% reduction of cell accumulation 3 days after transplantation compared to control (FIG. 5A). However, 7 days after transplantation after robust proliferation (FIG. 5C) the difference in cell accumulation between control and 6A6 treated mice was no longer significant (FIG. 5B).

Figure 6:
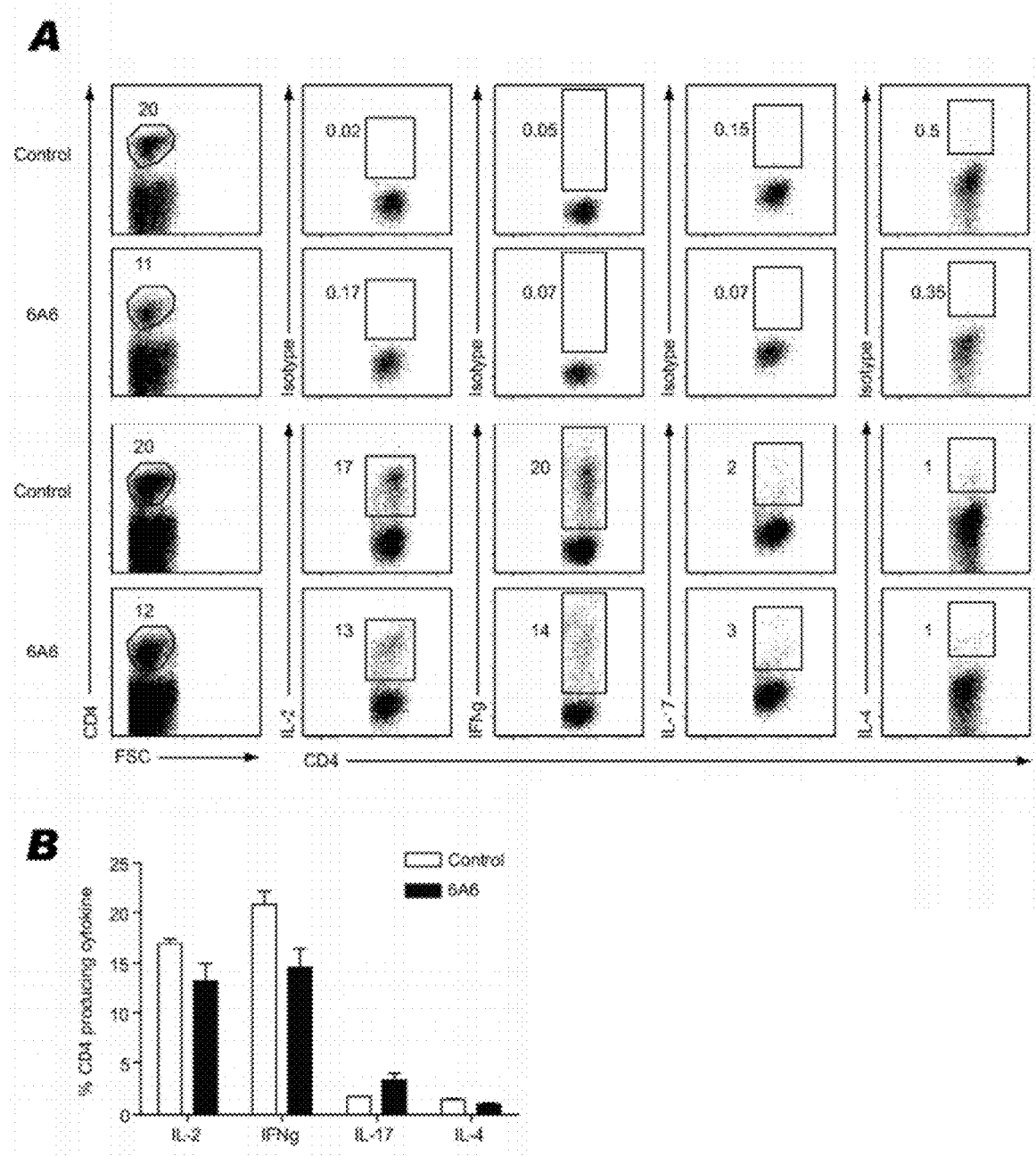
FIG. 6 depicts a series of graphs showing that 6A6 treatment does not change the cytokine production of donor CD4 T cells. CB6F1 (CD45.1-H-2 Kd+) mice were lethally irradiated and received $2.0\times10^7$ BMCs and $1.0\times10^7$ splenocytes from B6.SJL mice, and either control antibody or 6A6. 7 days after BMT splenocytes were harvested and stimulated with PMA/Ionomycin for 4 hours. Following restimulation cells were stained for CD4, and either IL-2, IFNγ, IL-17 and IL-4 or Isotype controls for the cytokines. (A) Plots show CD4+ cells and FSC, further gated on all CD4+ cells. The top two rows show isotype controls for control and 6A6 treated mice. The bottom two rows show the production of the indicated cytokine following either control or 6A6 treatment. (B) Same experiment as in (A). The graph shows the percentage of CD4+ cells producing the indicated cytokine.

CD4 T cell accumulation was reduced by approximately 70% on day 3 in mice treated with 6A6 (FIG. 5B), this decreased expansion in CD4 T cells persisted at day 7 with approximately a 50% reduction in the expansion of donor derived T cells in mice treated with 6A6 compared to PIP. Furthermore, to assay whether 6A6 treatment lead to an anergic phenotype of CD4 T cells, we measured IL-2 production from cells 7 days post transplantation. CD4 T cells from mice that received 6A6 treatment produced IL-2 similar to control treated mice (FIG. 6). These data indicate that 6A6 treatment does not induce anergy in CD4 T cells as they proliferate and produce IL-2. Furthermore, CD8 T cell expansion was unaffected with 6A6 treatment by day 7 post transplantation and CD4 T cell accumulation was only modestly affected.

GVHD is driven by a strong TH1 immune response and we sought to determine if treatment with 6A6 causes a skewing in the cytokine profile of CD4 T cells 7 days after BMT. Mice that were treated with control antibody produced mainly IFNγ, in addition, little IL-17 and IL-4 was produced by CD4 T cells which is the cytokine profile indicative of a strong TH1 response (FIG. 6). CD4 T cells from mice treated with 6A6 antibody displayed the same strong TH1 cytokine profile as control treated mice with slightly reduced IFNγ and IL-2 production (FIG. 6). The decrease in IFNγ production is possibly due to the curative affect of 6A6, yet no obvious skewing of the immune response occurred with no increase in IL-17 or IL-4 production.

Figure 7:
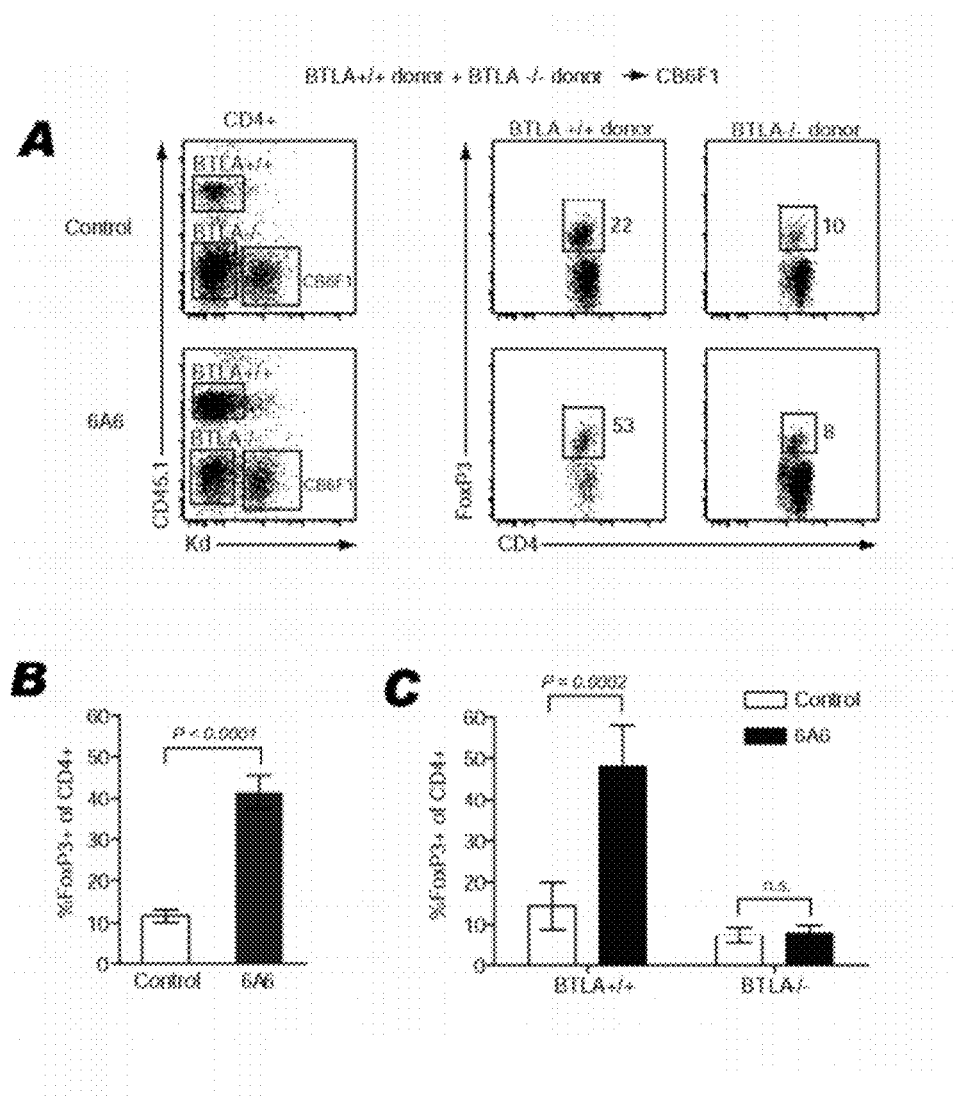
FIG. 7 depicts a series of graphs showing that direct engagement of BTLA on donor CD4 T cells leads to an increased frequency of CD4+ FoxP3+ cells. CB6F1 (CD45.1-H-2 Kd+) mice were lethally irradiated and received either $2.0\times10^7$ BMCs and $1.0\times10^7$ B6.SJL BTLA+/+ splenocytes alone (B) or a 1:1 mixture of B6.SJL BTLA+/+ (CD45.1+H-2 Kd−) and C57BL/6 BTLA−/− (CD45.1-H-2 Kd−) donor cells (A and C) with either a single 200 µg injection intraperitoneally of control antibody or 6A6. After 7 days splenocytes were stained for CD45.1, H-2 Kd, CD4, and intracellularly for FoxP3. (A) Shown are plots for CD45.1 and H-2 Kd (left) and CD4 and FoxP3 (right) gated on C57BL/6 BTLA−/− (CD4+CD45.1− H-2 Kd−) or C57BL/6 BTLA+/+ (CD4+ CD45.1+ H-2 Kd−) donor cell populations as indicated. Numbers represent the percentage of cells within the indicated gates. (B) Shown are the percentage of CD45.1+CD4+ FoxP3+ cells as a percentage of all CD45.1+CD4+B6.SJL BTLA+/+ derived donor cells. Data shown are mean±SEM (n=5). (C) Same experiment as in (A). Shown are the percentage of CD4+FoxP3+ cells as a percentage of all donor CD4+ cells from either B6.SJL BTLA+/+ mice (left) or from C57BL/6 BTLA−/− mice (right) that received either control antibody (open bars) or 6A6 (filled bars). Data shown are mean±SEM (n=5)

The only indication there is a difference in response when mice are treated with 6A6 is the slight reduction in proliferation and production of IL-2 by CD4 T cells. This phenotype is reminiscent of CD4+ T regulatory cells which selectively express the transcription factor forkhead box P3 (Foxp3) (36). Recently a significant role for regulatory T cells has been described for preventing GVHD in a manner similar to our observations following 6A6 treatment (37-40). To determine whether anti BTLA antibody treatment was preventing GVHD through modulation of T regulatory cells, we measured the expression of FoxP3 in CD4+ donor T cells 7 days after bone marrow transplantation (FIG. 7A). Mice treated with the control antibody PIP, which developed GVHD, had 12%±3% of donor CD4 T cells which expressed Foxp3 (FIG. 7B). By comparison, when 6A6 was used, there was a marked increase in the expression of Foxp3 (40%±5%) by donor derived CD4 T cells (FIG. 7B). Thus the increased frequency of Tregs 7 days following anti-BTLA treatment is in agreement with the modest reduction of accumulation and IL-2 production of CD4 T cells. As Tregs are potent suppressors of immune function it is likely the selective expansion of Tregs following 6A6 treatment that results in the prevention of GVHD.

BTLA is expressed by many cells of the hematopoietic system, thus it was not clear if 6A6 engagement on T cells was necessary for the increase in FoxP3 or if another cell such as an APC received a signal from 6A6 which resulted in priming of a CD4 T cell to become Tregs. Therefore we performed a mixed BMT with wildtype and BTLA-/- bone marrow and splenocytes. If 6A6 treatment directly induces Tregs there would be an increase in Tregs from the wildtype donors only, in contrast indirect induction of Tregs by an APC would result in an increase of Tregs from both wildtype and BTLA-/- donors. The increase in Tregs was observed in wildtype cells that were treated with 6A6 (FIGS. 7A & C). In contrast, cells from the BTLA-/- donor had no increase in Tregs following 6A6 treatment compared to mice receiving control antibody (FIGS. 7A & C). Therefore 6A6 administration at the time of BMT directly engages BTLA on CD4 T cells to preferentially increase the frequency of Tregs.

Example 7

Antibody Mechanism Expands Existing CD4 Treg Population

Figure 8:
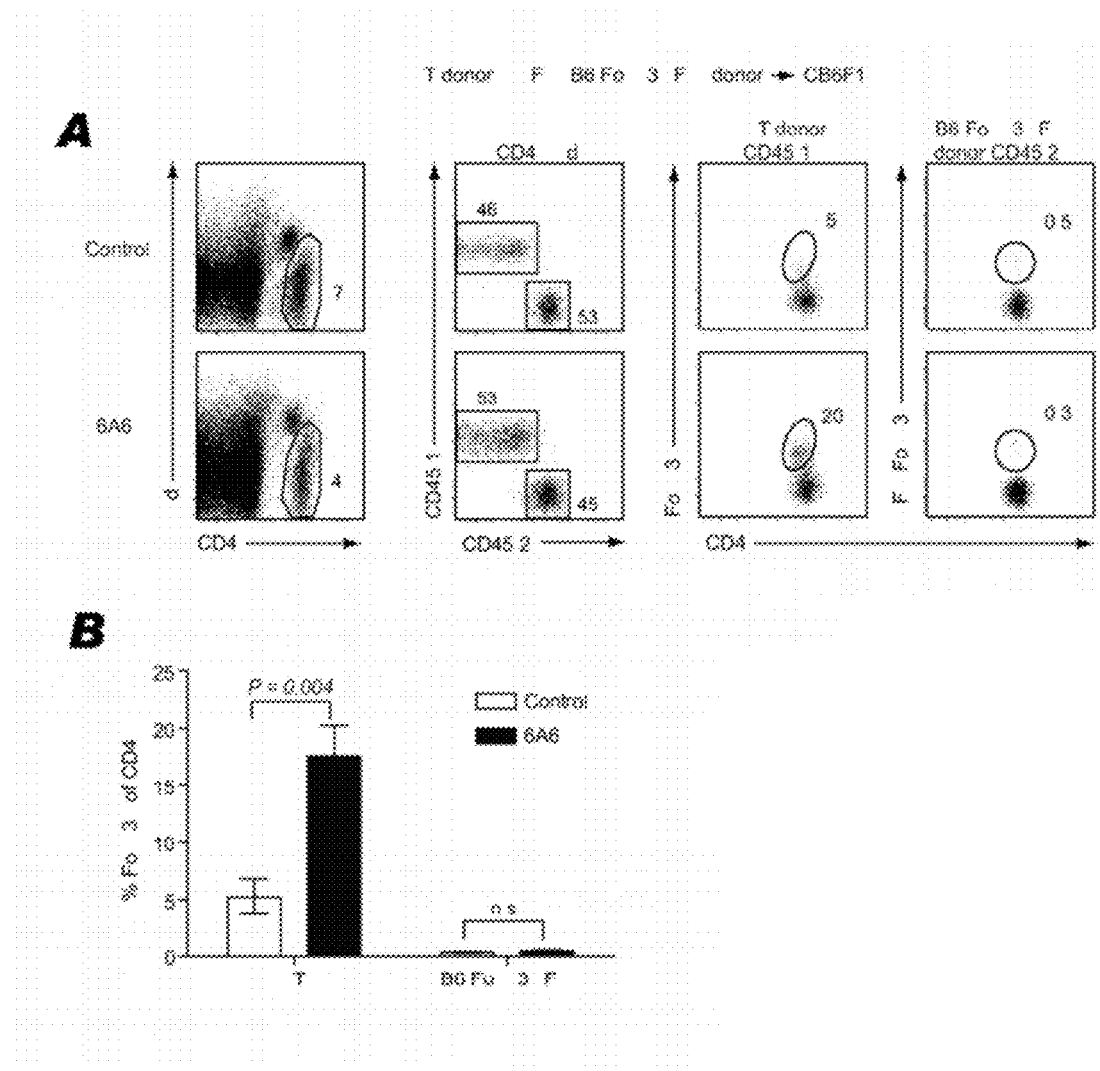
FIG. 8 depicts a series of graphs showing that anti BTLA treatment expands pre-existing Tregs within the BMT. CB6F1 (CD45.2+H-2 Kd+) mice were lethally irradiated and received $2.0\times10^7$ BMCs and $1.0\times10^7$ WT B6.SJL (CD45.1+ H-2 Kd−) splenocytes along with $1\times10^6$ purified CD4+ FoxP3− T cells from B6.FoxP3GFP mice (CD45.2+H-2 Kd−) with either a single 200 ug injection intraperitoneally of control antibody or 6A6. After 7 days splenocytes were stained for CD45.1, CD45.2, H-2 Kd, CD4, and either intracellularly for FoxP3, or FoxP3 expression was determined by GFP expression. (A) Donor cells are identified by lacking H2-Kd and expressing CD4, then expression of CD45.2 or CD45.1 is used to determine the origin of the donor. Expression of intracellular FoxP3 within CD4 T cells from the WT donor (CD5.1+) is shown. Expression of FoxP3 as reported by GFP from the B6.FoxP3GFP donor (CD45.2+) is shown. (B) Same experiment as in (A). Shown are the percentage of CD4+FoxP3+ cells as a percentage of all donor CD4+ cells from either WT donors (left) or from B6.FoxP3GFP donors (right) that received either control antibody (open bars) or 6A6 (filled bars). Data shown are mean±SEM (n=5)
Figure 9:
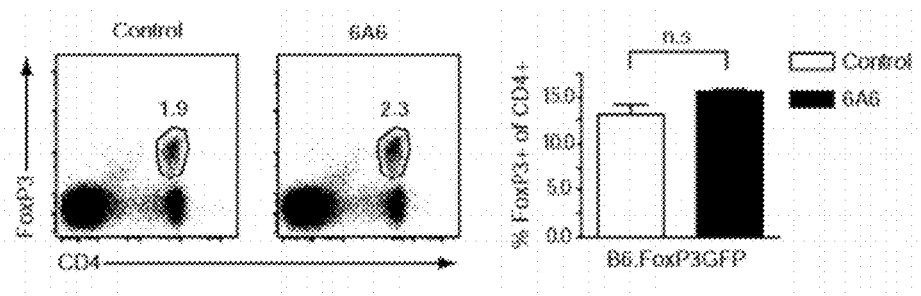
FIG. 9 depicts a series of graphs showing that 6A6 does not expand steady state Tregs. B6.FoxP3GFP mice were injected with 200 ug of either control antibody or 6A6 intraperitoneally and splenocytes were harvested 6 days later. Cells were stained with CD4 and FoxP3 expression was determined by GFP expression. (A) Plots showing the percentage of all cells that express CD4 and FoxP3 following control antibody (right) or 6A6 treatment (left). (B) Same experiment as in (A) showing the percent of FoxP3+ cells within CD4+ T cells.

The expansion of Tregs following 6A6 treatment could be the result of either the expansion of pre-existing Tregs in the splenic portion of the BMT or through peripheral conversion of naïve CD4 T cells into FoxP3+ Tregs (41). To ascertain whether 6A6 could induce peripheral conversion of naïve CD4 T cells into Tregs we added FoxP3-negative CD4+ cells from B6.FoxP3-GFP mice (42) and mixed them with the normal BMT. Treatment with control antibody increased the frequency of donor CD4+FoxP3+ cells in the wildtype unpurified splenocyte fraction of the BMT as previously observed (FIGS. 8A & B). However, the population of donor CD4 T cells obtained from B6.FoxP3GFPKI which originally were CD4+FoxP3- failed to increase their expression of FoxP3 as indicated by GFP expression 7 days following 6A6 treatment (FIGS. 8A & B). The expansion of pre-existing Tregs likely requires T cell activation because 6A6 treatment directly into otherwise unmanipulated B6.FoxP3GFPKI mice did not preferentially increase the frequency of CD4+FoxP3+ cells 6 days following when compared to control mice (FIG. 9). In total, these results indicate that a single administration of 6A6 at the time of bone marrow transplantation leads to the complete prevention of GVHD and the concomitant expansion of pre-existing CD4 T regulatory cells that are donor derived.

This study has demonstrated that although the natural progression of GVHD does not normally engage BTLA in the parental into F1 irradiated model, direct BTLA engagement using a non-depleting anti-BTLA antibody can permanently prevent GVHD and increase the frequency of pre-existing donor derived regulatory T cells. Once GVHD has been established anti-BTLA treatment had no effect suggesting early expansion of Tregs is important for achieving a suppressive environment of alloreactive donor T cells.

Material and Methods

Mice and bone marrow transplantation B6.SJL-Ptprca Pep3b/BoyJ (B6.SJL), C57BL/6, and C57BL/6×BALB/c F1 (CB6F1) mice were obtained from The Jackson Laboratory (Bar Harbor, Me.) or bred in our facility. BTLA$^{-/-}$ (23), Hvem$^{-/-}$ (43), and FoxP3GFP (42) mice were backcrossed to C57BL/6 for at least nine generations. Mice were 12-18 weeks old and female. All mice were kept under special pathogen-free conditions.

Cell transplantation and assessment of GVHD Mice received transplants according to a standard protocol as previously described (30). Briefly, bone marrow cells were harvested by flushing tibia and femurs of donor mice. For GVHD induction, CB6F1 (H-2$^{b/d}$) recipients were lethally irradiated with 9 Gy total body irradiation (TBI) using a 137Cs source at a dose rate of ~70 cGy/minute and reconstituted with bone marrow cells (BMCs) and additional splenocytes (2×10$^7$ BMCs and 1×10$^7$ splenocytes) from indicated donors (H-2$^d$). GVHD was monitored by calculating the loss in total body weight. Body weights were measured before transplantation and 3 times a week after transplantation. Clinical GVHD intensity was scored by assessing weight loss, posture, activity, fur texture, and skin integrity (24). Histopathologic analyses of the bowel were performed on hematoxylin and eosin (H&E)—stained tissue. Microscopic analyses were performed with a BX51 light microscope (Olympus, Hamburg, Germany) equipped with a 40×/0.75 NA objective lens and a DP70 camera (Olympus) using Cell A Analysis software (Olympus Software Imaging Solutions 1986-2007, Muenster, Germany). Experiments were performed in accordance with national and institutional guidelines.

CFSE labeling and Flow Cytometery Cells were labeled with CFSE (carboxyfluorescein diacetate succinimidyl diester; Sigma-Aldrich) by being incubated for 8 min at 25° C. with 1 μM CFSE at a density of 40×10$^6$ cells per ml in PBS. Cells were incubated for 1 min with an equal volume of FCS and were washed twice with media containing 10% (vol/vol)

FCS. 50×10$^6$ total cells were injected IV per mouse. Single cell suspensions from spleens were analyzed by flow cytometry using the following antibodies for detection: Kd-FITC (SF1-1.1), CD4-PECy7 and APC (RM4-5), anti-Armenian and Syrian hamster IgG cocktail-PE, CD19-APC (1D3) purchased from BD Pharmingen. Additional antibodies purchased from eBioscience were also used: CD45.1-PECy7 and APC (A20), CD8-APC AlexaFluor 750 (53-6.7), CD4-APC AlexaFluor 750 (RM4-5). Intracellular FoxP3 was detected using eBioscience Mouse Regulatory T cell staining Kit with FoxP3-PE or APC (FJK-16s). For intracellular cytokine staining splenocytes were first restimulated with PMA/ionomycin for 4 hours and were stained with antibodies to surface markers followed by fixation with 2% formaldehyde for 15 minutes at room temperature. Cells were then washed once in 0.05% saponin and stained with anti-cytokine antibodies (anti IL-17 FITC, IL-2 PE, IFNg PE-Cy7 and IL-4 APC in 0.5% saponin. All flow cytometry data were collected on a FACS-Canto II (BD Biosciences) and were analyzed with FlowJo software (Tree Star).

Administration of antibody In some experiments mice received a single intraperitoneal injection of 10-20 µg/g body weight of the IgG1 hamster injection of monoclonal anti-BTLA antibody 6A6, the IgGK mouse monoclonal anti-BTLA antibody 6F7 (Hurchla, 2005) or the hamster monoclonal anti-GST antibody PIP (Gronowski, 1999) at indicated time points.

Statistical analysis A Student's unpaired two-tailed t-test was used for statistical analyses of body weight data. Differences with P values of 0.05 or less are considered significant.

REFERENCE LIST

1. Alexander, S. I. et al., Brief report: Chimerism and tolerance in a recipient of a deceased-donor liver transplant. New England Journal of Medicine 358, 369-374 (2008).
2. Kawai, T. et al., Brief report: HLA-mismatched renal transplantation without maintenance immunosuppression. New England Journal of Medicine 358, 353-361 (2008).
3. Scandling, J. D. et al., Brief report: Tolerance and chimerism after renal and hematopoietic-cell transplantation. New England Journal of Medicine 358, 362-368 (2008).
4. Blazar, B. R. et al., Infusion of anti-B7.1 (CD80) and anti-B7.2 (CD86) monoclonal antibodies inhibits murine graft-versus-host disease lethality in part via direct effects on CD4+ and CD8+ T cells. Journal of Immunology 157, 3250-3259 (1996).
5. Lang, T. J. et al., In vivo CD86 blockade inhibits CD4+ T cell activation, whereas CD80 blockade potentiates CD8+ T cell activation and CTL effector function. The Journal of Immunology 168, 3786-3792 (2002).
6. Hakim, F. T. et al., Acute graft-versus-host reaction can be aborted by blockade of costimulatory molecules. The Journal of Immunology 155, 1757-1766 (1995).
7. Via, C. S. et al., Differential effect of CTLA4Ig on murine graft-versus-host disease (GVHD) development—CTLA4Ig prevents both acute and chronic GVHD development but reverses only chronic GVHD. Journal of Immunology 157, 4258-4267 (1996).
8. Yu, X. Z., Martin, P. J., and Anasetti, C. Role of CD28 in acute graft-versus-host disease. Blood 92, 2963-2970 (1998).
9. Speiser, D. E. et al., Acute graft-versus-host disease without costimulation via CD28. Transplantation 63, 1042-1044 (1997).
10. Ogawa, S. et al., Opposing effects of anti-activation-inducible lymphocyte-immunomodulatory molecule/inducible costimulator antibody on the development of acute versus chronic graft-versus-host disease. Journal of Immunology 167, 5741-5748 (2001).
11. Hubbard, V. M. et al., Absence of inducible costimulator on alloreactive T cells reduces graft versus host disease and induces Th2 deviation. Blood 106, 3285-3292 (2005).
12. Taylor, P. A. et al., Targeting of inducible costimulator (ICOS) expressed on alloreactive T cells down-regulates graft-versus-host disease (GVHD) and facilitates engraftment of allogeneic bone marrow (BM). Blood 105, 3372-3380 (2005).
13. Tamada, K. et al., LIGHT, a TNF-like molecule, costimulates T cell proliferation and is required for dendritic cell-mediated allogeneic T cell response. J. Immunol. 164, 4105-4110 (2000).
14. Tamada, K. et al., Modulation of T-cell-mediated immunity in tumor and graft-versus-host disease models through the LIGHT co-stimulatory pathway. Nat. Med. 6, 283-289 (2000).
15. Tamada, K. et al., Blockade of LIGHT/LT beta and CD40 signaling induces allospecific T cell anergy, preventing graft-versus-host disease. Journal of Clinical Investigation 109, 549-557 (2002).
16. Xu, Y. et al., Selective targeting of the LIGHT-HVEM co-stimulatory system for the treatment of graft-versus-host disease. Blood (2006).
17. Tsukada, N. et al., Blockade of CD134 (OX40)-CD134L interaction ameliorates lethal acute graft-versus-host disease in a murine model of allogeneic bone marrow transplantation. Blood 95, 2434-2439 (2000).
18. Blazar, B. R. et al., Ligation of OX40 (CD134) regulates graft-versus-host disease (GVHD) and graft rejection in allogeneic bone marrow transplant recipients. Blood 101, 3741-3748 (2003).
19. Blazar, B. R. et al., CD30/CD30 ligand (CD153) interaction regulates CD4(+) T cell-mediated graft-versus-host disease. Journal of Immunology 173, 2933-2941 (2004).
20. Blazar, B. R. et al., Blockade of programmed death-1 engagement accelerates graft-versus-host disease lethality by an IFN-gamma-dependent mechanism. Journal of Immunology 171, 1272-1277 (2003).
21. Hurchla, M. A., Sedy, J. R., and Murphy, K. M. Unexpected role of B and T lymphocyte attenuator in sustaining cell survival during chronic allostimulation. The Journal of Immunology 178, 6073-6082 (2007).
22. Hurchla, M. A. et al., B and T lymphocyte attenuator exhibits structural and expression polymorphisms and is highly induced in anergic CD4(+) T cells. Journal of Immunology 174, 3377-3385 (2005).
23. Watanabe, N. et al., BTLA is a lymphocyte inhibitory receptor with similarities to CTLA-4 and PD-1. Nat. Immunol. 4, 670-679 (2003).
24. Cooke, K. R. et al., An experimental model of idiopathic pneumonia syndrome after bone marrow transplantation 0.1. The roles of minor H antigens and endotoxin. Blood 88, 3230-3239 (1996).
25. Gavrieli, M. et al., Characterization of phosphotyrosine binding motifs in the cytoplasmic domain of B and T lymphocyte attenuator required for association with protein tyrosine phosphatases SHP-1 and SHP-2. Biochem Biophys. Res Commun. 312, 1236-1243 (2003).
26. Chemnitz, J. M. et al., B and T lymphocyte attenuator-mediated signal transduction provides a potent inhibitory signal to primary human CD4 T cells that can be initiated by multiple phosphotyrosine motifs. The Journal of Immunology 176, 6603-6614 (2006).

27. Steinberg, M. W. et al., A crucial role for HVEM and BTLA in preventing intestinal inflammation. J. Exp. Med. 205, 1463-1476 (2008).
28. Lepenies, B. et al., Ligation of B and T lymphocyte attenuator prevents the genesis of experimental cerebral malaria. The Journal of Immunology 179, 4093-4100 (2007).
29. Gronowski, A. M. et al., Baculovirus stimulates antiviral effects in mammalian cells. Journal of Virology 73, 9944-9951 (1999).
30. Stelljes, M. et al., Clinical molecular imaging in intestinal graft-versus-host disease: mapping of disease activity, prediction, and monitoring of treatment efficiency by positron emission tomography. Blood 111, 2909-2918 (2008).
31. Sedy, J. R. et al., B and T lymphocyte attenuator regulates T cell activation through interaction with herpesvirus entry mediator. Nat. Immunol. 6, 90-98 (2005).
32. Gonzalez, L. C. et al., A coreceptor interaction between the CD28 and TNF receptor family members B and T lymphocyte attenuator and herpesvirus entry mediator. Proc. Natl. Acad. Sci U.S.A 102, 1116-1121 (2005).
33. Wu, T. H. et al., B and T lymphocyte attenuator interacts with CD3zeta and inhibits tyrosine phosphorylation of TCRzeta complex during T-cell activation. Immunol Cell Biol (2007).
34. Gavrieli, M. and Murphy, K. M. Association of Grb-2 and PI3K p85 with phosphotyrosile peptides derived from BTLA. Biochem Biophys. Res Commun. 345, 1440-1445 (2006).
35. Liu, X. K. et al., Cutting Edge: A Critical Role of B and T Lymphocyte Attenuator in Peripheral T Cell Tolerance Induction. Journal of Immunology 182, 4516-4520 (2009).
36. Hori, S., Nomura, T., and Sakaguchi, S. Control of regulatory T cell development by the transcription factor Foxp3. Science 299, 1057-1061 (2003).
37. Taylor, P. A., Lees, C. J., and Blazar, B. R. The infusion of ex vivo activated and expanded CD4(+) CD25(+) immune regulatory cells inhibits graft-versus-host disease lethality. Blood 99, 3493-3499 (2002).
38. Cohen, J. L. et al., CD4(+) CD25(+) immunoregulatory T cells: New therapeutics for graft-versus-host disease. Journal of Experimental Medicine 196, 401-406 (2002).
39. Hoffmann, P. et al., Donor-type CD4(+) CD25(+) regulatory T cells suppress lethal acute graft-versus-host disease after allogeneic bone marrow transplantation. Journal of Experimental Medicine 196, 389-399 (2002).
40. Edinger, M. et al., CD4(+) CD25(+) regulatory T cells preserve graft-versus-tumor activity while inhibiting graft-versus-host disease after bone marrow transplantation. Nature Medicine 9, 1144-1150 (2003).
41. Chen, W. et al., Conversion of Peripheral CD4+CD25− Naive T cells to CD4+CD25+Regulatory T cells by TGF-beta Induction of Transcription Factor FoxP3. J. Exp. Med. 198, 1875-1886 (2003).
42. Fontenot, J. D. et al., Regulatory T cell lineage specification by the forkhead transcription factor FoxP3. Immunity 22, 329-341 (2005).
43. Wang, Y. et al., The role of herpesvirus entry mediator as a negative regulator of T cell-mediated responses. J. Clin. Invest 115, 711-717 (2005).

What is claimed is:

1. A method for treating GVHD, the method comprising administering an agonistic anti-BTLA antibody that does not deplete T cells that express BTLA to a subject at substantially the same time the subject is exposed to a graft.

2. The method of claim 1, wherein the antibody is administered at the same time as the graft exposure.
3. The method of claim 1, wherein the antibody is administered before the graft exposure.
4. The method of claim 1, wherein the antibody is administered within one week of the graft exposure.
5. The method of claim 1, wherein the antibody expands a pre-existing Treg cell population.
6. The method of claim 1, wherein the antibody is administered once.
7. The method of claim 6, wherein the antibody is administered once, and at the time of graft exposure.
8. A method for inducing in vivo tolerance to a foreign bone marrow in a subject, the method comprising administering an agonistic anti-BTLA antibody to a subject undergoing a bone marrow transplant at substantially the same time as the foreign tissue exposure.
9. The method of claim 8, wherein the immune system of the subject is not systemically suppressed.
10. The method of claim 8, wherein the antibody does not deplete T cells.
11. The method of claim 8, wherein the antibody is administered at the same time as the foreign tissue exposure.
12. The method of claim 8, wherein the antibody is administered before the foreign tissue exposure.
13. The method of claim 8, wherein the antibody is administered within one week of the foreign tissue exposure.
14. The method of claim 8, wherein the antibody expands a pre-existing Treg cell population.
15. The method of claim 8, wherein the antibody is administered once.
16. The method of claim 15, wherein the antibody is administered once, and at the time of foreign tissue exposure.
17. A method for treating GVHD, the method comprising administering an agonistic anti-BTLA antibody to a subject undergoing a bone marrow transplant at substantially the same time the subject is exposed to a graft.
18. The method of claim 17, wherein the antibody does not deplete T cells.
19. The method of claim 17, wherein the antibody is administered at the same time as the graft exposure.
20. The method of claim 17, wherein the antibody is administered before the graft exposure.
21. The method of claim 17, wherein the antibody is administered within one week of the graft exposure.
22. The method of claim 17, wherein the antibody expands a pre-existing Treg cell population.
23. The method of claim 17, wherein the antibody is administered once.
24. The method of claim 23, wherein the antibody is administered once, and at the time of graft exposure.
25. A method for treating GVHD, the method comprising administering a single dose of an agonistic anti-BTLA antibody to a subject at substantially the same time the subject is exposed to a graft.
26. The method of claim 25, wherein the antibody does not deplete T cells.
27. The method of claim 25, wherein the antibody is administered at the same time as the graft exposure.
28. The method of claim 25, wherein the antibody is administered before the graft exposure.
29. The method of claim 25, wherein the antibody is administered within one week of the graft exposure.

* * * * *